(12) United States Patent
Huang et al.

(10) Patent No.: US 9,647,215 B2
(45) Date of Patent: May 9, 2017

(54) ORGANIC ELECTRONIC MATERIAL

(71) Applicants: GUANGDONG AGLAIA OPTOELECTRONIC MATERIALS CO., LTD., Foshan, Guangdong (CN); BEIJING AGLAIA TECHNOLOGY DEVELOPMENT CO., LTD., Beijing (CN)

(72) Inventors: Jinhai Huang, Beijing (CN); Lifei Cai, Beijing (CN); Lei Dai, Beijing (CN); Kam-Hung Low, Foshan (CN)

(73) Assignees: GUANGDONG AGLAIA OPTOELECTRONIC MATERIALS CO., LTD., Foshan (CN); BEIJING AGLAIA TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 14/787,266

(22) PCT Filed: Apr. 25, 2014

(86) PCT No.: PCT/CN2014/076285
§ 371 (c)(1),
(2) Date: Oct. 26, 2015

(87) PCT Pub. No.: WO2014/173324
PCT Pub. Date: Oct. 30, 2014

(65) Prior Publication Data
US 2016/0087222 A1  Mar. 24, 2016

(30) Foreign Application Priority Data

Apr. 27, 2013  (CN) .......................... 2013 1 0154057

(51) Int. Cl.
  *C07D 219/08* (2006.01)
  *C07D 401/14* (2006.01)
  *H01L 51/00* (2006.01)
  *C07D 405/14* (2006.01)
  *C07D 409/14* (2006.01)
  *C09K 11/06* (2006.01)
  *H01L 51/50* (2006.01)

(52) U.S. Cl.
  CPC ........ *H01L 51/0061* (2013.01); *C07D 219/08* (2013.01); *C07D 401/14* (2013.01); *C07D 405/14* (2013.01); *C07D 409/14* (2013.01); *C09K 11/06* (2013.01); *H01L 51/006* (2013.01); *H01L 51/0059* (2013.01); *C09K 2211/1007* (2013.01); *C09K 2211/1029* (2013.01); *H01L 51/0072* (2013.01); *H01L 51/0073* (2013.01); *H01L 51/0074* (2013.01); *H01L 51/5056* (2013.01); *H01L 51/5088* (2013.01); *Y02E 10/549* (2013.01); *Y02P 70/521* (2015.11)

(58) Field of Classification Search
None
See application file for complete search history.

(56) References Cited

FOREIGN PATENT DOCUMENTS

| CN | 1906267 A | 1/2007 |
|---|---|---|
| CN | 101405255 A | 4/2009 |
| CN | 101679150 A | 3/2010 |
| KR | 20100006072 A | 1/2010 |

*Primary Examiner* — Heidi Reese
(74) *Attorney, Agent, or Firm* — Maschoff Brennan

(57) ABSTRACT

The present invention also relates to an organic electronic material with the structure of formula (I). It is a kind of hole transport and injection material with good thermal stability, high hole mobility and excellent solubility. The OLEDs prepared thereof have the advantages such as good light emitting efficiency, excellent color purity and long lifetime.

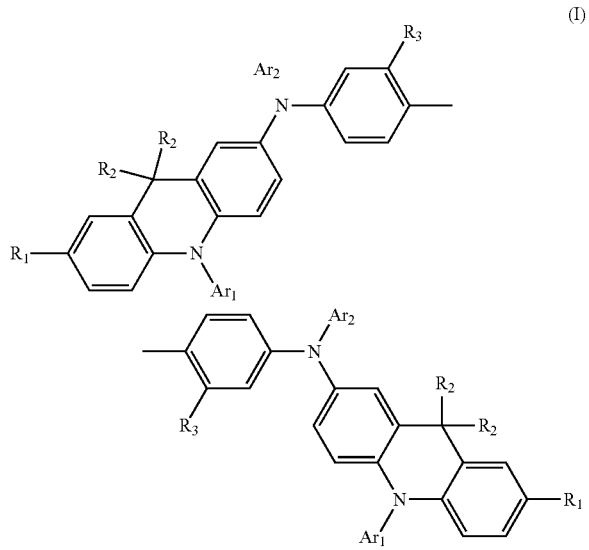

16 Claims, 3 Drawing Sheets

ORGANIC ELECTRONIC MATERIAL

TECHNICAL FIELD

This invention relates to a new type of organic electronic material. By deposited into or spun into thin film through vacuum evaporation, it is used in organic light emitting diodes. It belongs to the organic light-emitting device (OLED) field.

BACKGROUND ART

OLED, as a new type of display technology, has unique advantages such as self-illumination, wide viewing angle, low power consumption, high efficiency, thin, rich colors, fast response, extensive application temperature, low drive voltage, used to make flexible, bendable and transparent display panel and environmental friendliness, etc. Therefore, OLED technology can be applied to flat panel displays and new generation of lighting, or can be used as backlight of LCD.

OLED is a device made through spin-coating or depositing a layer of organic material between two metal electrodes. A classic three-layer OLED comprises a hole transport layer, a light emitting layer and an electron transport layer. The holes generating from the anode through the hole transport layer and the electrons generating from the cathode through the electron transport layer combine to form excitons in the light emitting layer, emitting light. By changing the material of the light emitting layer, the OLED can emit red light, green light and blue light, and OLED can also emit the white light through material matching in the light emitting layer.

However, the applications of existing OLEDs are restricted by low efficiency and short service life, therefore, these constraints must be avoided. Lowering the energy barrier between the hole injecting/transport material and the light emitting material and improving the thermal stability of hole transport material can facilitate to improve the efficiency and enhance the life of OLEDs; besides, due to poor solubility of small molecule hole-injecting/transport material, the device can be prepared by depositing, which is not conducive to its commercialized use. Therefore, the large-scale applications of devices can be improved by developing the materials with high hole mobility, to achieve the spin-coating and ink-jet printing.

The existing hole injecting material copper phthalocyanine (CuPc) is not environmentally friendly due to its slow degradation and high energy consumption for preparation. The common hole transport materials TPD and NPB have good hole mobility, $1.0*10^{-3}$ and $5.1*10^{-4}$ $cm^2V^{-1}S^{-1}$ respectively, but their glass transition temperatures are 65° C. and 98° C. respectively, and their stability cannot meet application requirements of OLED. Thus, it is necessary to develop efficient and stable OEL material, to produce highly efficient and stable OLEDs.

SUMMARY OF THE INVENTION

In the present invention, a series of hole transport and injecting materials with good thermal stability, high hole mobility rate and good solubility are provided, to overcome the deficiencies of the above compounds. OLEDs produced by these materials have the advantages such as good EL efficiency, excellent color purity and long lifetime.

An organic electronic material has the following structural formula (I):

Structural formula I

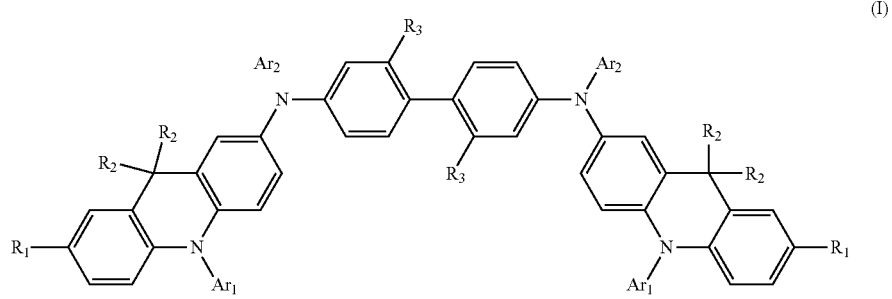

(I)

Wherein, $R_1$-$R_3$ independently represent hydrogen, deuterium, halogen, cyano, nitro, C1-C8 alkyl, C1-C8 alkoxy, C6-C30 aryl unsubstituted or substituted by one or more substituent group R, C3-C30 heteroaryl containing one or more heteroatoms unsubstituted or substituted by one or more substituent group R, C2-C8 alkenyl unsubstituted or substituted by one or more substituent group R, C2-C8 alkynyl unsubstituted or substituted by one or more substituent group R, C8-C30 diaryl vinyl unsubstituted or substituted by one or more substituent group R, C8-C30 diaryl ethynyl, trialkyl silicon unsubstituted or substituted by one or more substituent group R, C6-C30 triaryl silicon unsubstituted or substituted by one or more substituent group R, C6-C30 diaryl phosphonoso unsubstituted or substituted by one or more substituent group R, C6-C30 aryl carbonyl unsubstituted or substituted by one or more substituent group R, C6-C30 aryl sulfenyl unsubstituted or substituted by one or more substituent group R, C6-C30 aryl fused ring unsubstituted or substituted by one or more substituent group R, C6-C30 substituted or unsubstituted heteroatom-containing aryl fused ring, C6-C30 carbazolyl unsubstituted or substituted by one or more substituent group R, C6-C30 diaryl amine unsubstituted or substituted by one or more substituent group R, or a spiral structure formed between two $R_2$ groups, and the said heteroatoms are B, O, S, N, Se;

$Ar_1$-$Ar_2$ represent independently C6-C30 aryl containing one or more substituent group R, aryl fused ring unsubstituted or substituted by one or more substituent group R, C6-C30 carbazolyl unsubstituted or substituted by one or more substituent group R, C6-C30 tri-aromatic amine unsubstituted or substituted by one or more substituent group R.

Wherein, R represent independently alkyl, five- or six-membered ring aryl, alkoxy, deuterium, halogen, cyano, nitro, amino.

Preferably, $R_1$-$R_3$ are independently selected from hydrogen, halo, C1-C8 alkyl, C6-C30 phenyl group unsubstituted or substituted by one or more substituent group R, diaryl amine unsubstituted or substituted by one or more substituent group R, C6-C30 aryl fused ring unsubstituted or substituted by one or more substituent group R, C6-C30 carbazolyl unsubstituted or substituted by one or more substituent group R, or two $R_2$ form a spirofluorene structure; $Ar_1$-$Ar_2$ represent independently C6-C30 aryl containing one or more substituent group R, aryl fused ring unsubstituted or substituted by one or more substituent group R, C6-C30 carbazolyl unsubstituted or substituted by one or more substituent group R, C6-C30 tri-aromatic amine unsubstituted or substituted by one or more substituent group R, wherein R independently represents an alkyl group, a five- or six-membered ring of aryl, alkoxy, halogen.

Further preferably, wherein $R_1$-$R_8$ are independently selected from hydrogen, C1-C8 alkyl group, one or more C1-C3 alkyl, C1-C3 alkoxy, aryl-substituted or unsubstituted phenyl, one or more C1-C3 alkyl, C1-C3 alkoxy, aryl-substituted or unsubstituted naphthyl, one or more C1-C3 alkyl, C1-C3 alkoxy, aryl-substituted or unsubstituted carbazolyl or a spiral structure is formed between two $R_2$ groups.

Further preferably, wherein $R_1$, $R_2$ are independently selected from hydrogen, methyl, ethyl, propyl, isopropyl, butyl, t-butyl, n-pentyl, isopentyl, n-hexyl, isohexyl, cyclohexyl, n-octyl, isooctyl, C1-C3 alkyl substituted or unsubstituted phenyl, C1-C3 alkoxy substituted or unsubstituted phenyl, naphthyl or a spiral structure is formed between two $R_2$ groups, one or more methyl, phenyl substituted or unsubstituted diaryl amine, one or more methyl, phenyl substituted or unsubstituted carbazolyl. $R_3$ is independently selected from hydrogen, C1-C8 alkyl, C1-C3 substituted or unsubstituted phenyl.

Further preferably, wherein $R_1$, $R_2$ are independently selected from hydrogen, methyl, ethyl, propyl, isopropyl, butyl, t-butyl, n-pentyl, isopentyl, n-hexyl, isohexyl, cyclohexyl, n-octyl, iso-octyl, phenyl, tolyl, of which, $R_3$ is independently selected from hydrogen, C1-C3 alkyl, C1-C3 alkyl substituted or unsubstituted phenyl.

Most preferably, wherein $R_3$ is preferably hydrogen, methyl, phenyl, $R_1$, $R_2$ are independently selected from hydrogen, methyl, t-butyl, phenyl, R1, R2 are independently selected to form a spiro structure between hydrogen, methyl, t-butyl, phenyl or a spiral structure is formed between two $R_2$ groups. $Ar_1$-$Ar_2$ are independently expressed as any one of the groups in the table below.

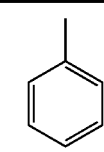

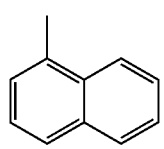

-continued

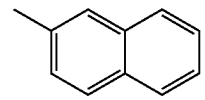

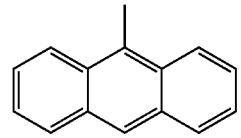

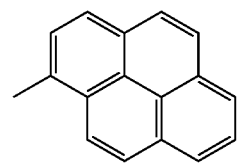 [SMILES: Cc1ccc2ccc3cccc4ccc1c2c34]

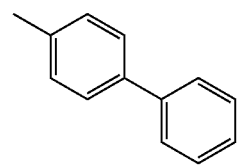

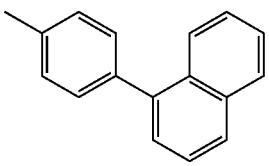 [SMILES: Cc1ccc(-c2cccc3ccccc23)cc1]

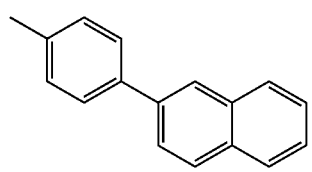 [SMILES: Cc1ccc(-c2ccc3ccccc3c2)cc1]

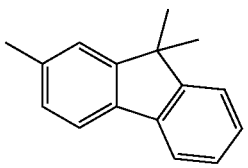 [SMILES: Cc1ccc2c(c1)C(C)(C)c1ccccc1-2]

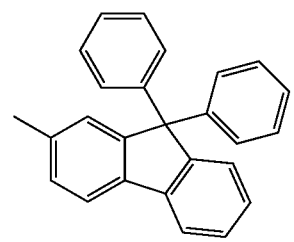 [SMILES: Cc1ccc2c(c1)C(c1ccccc1)(c1ccccc1)c1ccccc1-2]

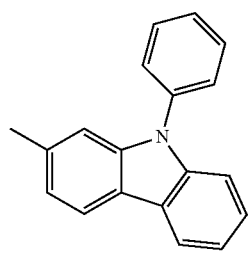 [SMILES: Cc1ccc2c3ccccc3n(-c3ccccc3)c2c1]
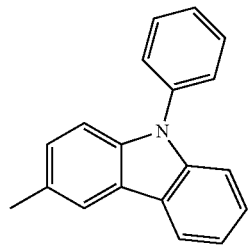 [SMILES: Cc1ccc2c(c1)c1ccccc1n2-c1ccccc1]
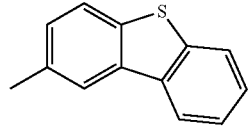
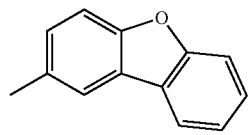
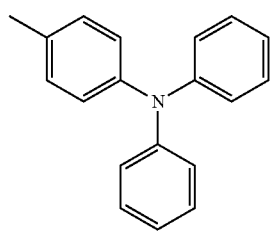 [SMILES: Cc1ccc(N(c2ccccc2)c2ccccc2)cc1]
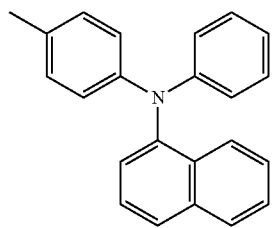 [SMILES: Cc1ccc(N(c2ccccc2)c2cccc3ccccc23)cc1]
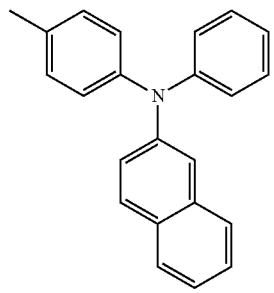 [SMILES: Cc1ccc(N(c2ccccc2)c2ccc3ccccc3c2)cc1]
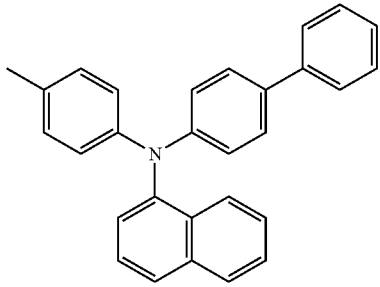 [SMILES: Cc1ccc(N(c2ccc(-c3ccccc3)cc2)c2cccc3ccccc23)cc1]
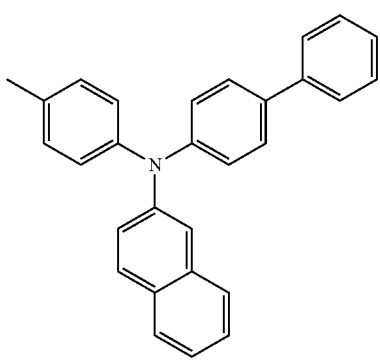 [SMILES: Cc1ccc(N(c2ccc(-c3ccccc3)cc2)c2ccc3ccccc3c2)cc1]
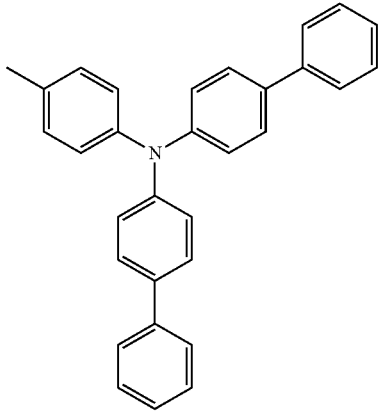 [SMILES: Cc1ccc(N(c2ccc(-c3ccccc3)cc2)c2ccc(-c3ccccc3)cc2)cc1]
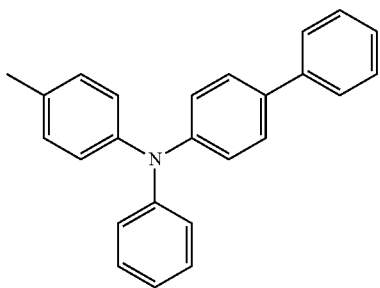 [SMILES: Cc1ccc(N(c2ccccc2)c2ccc(-c3ccccc3)cc2)cc1]

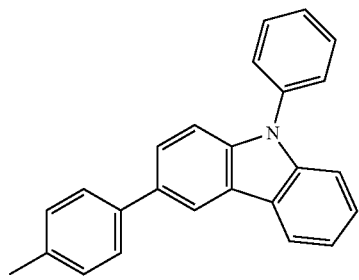 [SMILES: Cc1ccc(-c2ccc3c(c2)c2ccccc2n3-c2ccccc2)cc1]
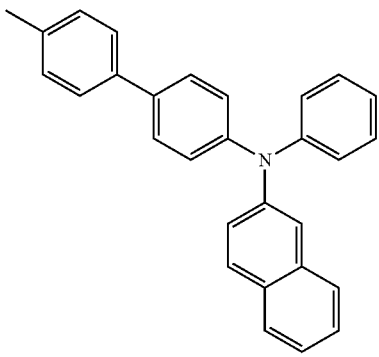
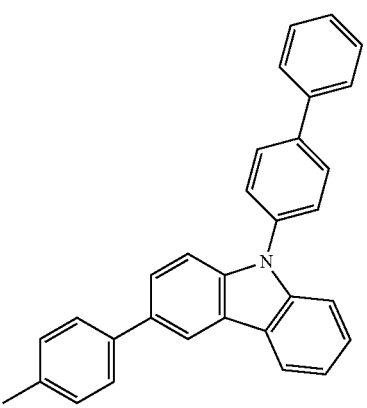 [SMILES: Cc1ccc(-c2ccc3c(c2)c2ccccc2n3-c2ccc(-c3ccccc3)cc2)cc1]
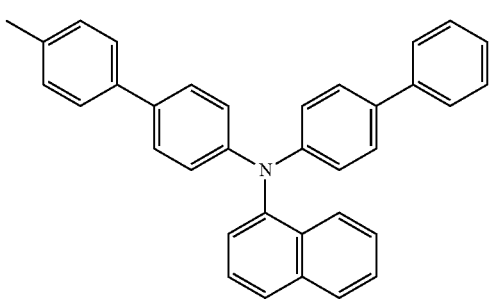
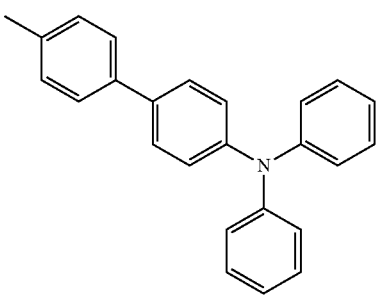 [SMILES: Cc1ccc(-c2ccc(N(c3ccccc3)c3ccccc3)cc2)cc1]
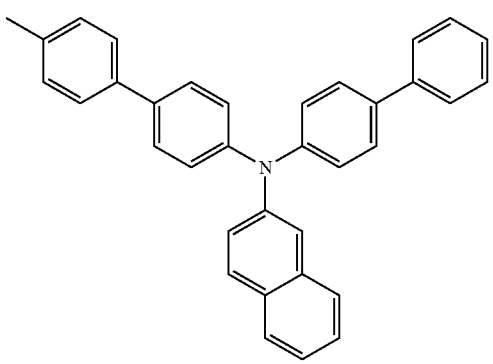
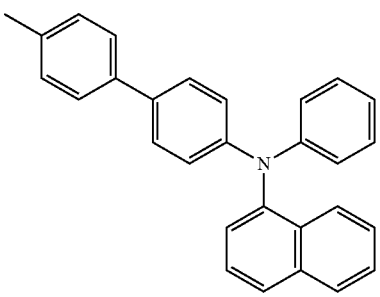 [SMILES: Cc1ccc(-c2ccc(N(c3ccccc3)c3cccc4ccccc34)cc2)cc1]
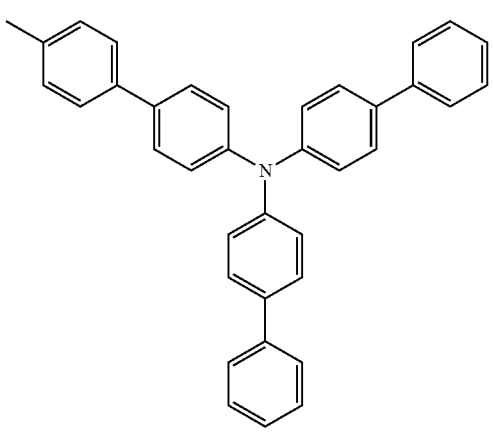 [SMILES: Cc1ccc(-c2ccc(N(c3ccc(-c4ccccc4)cc3)c3ccc(-c4ccccc4)cc3)cc2)cc1]

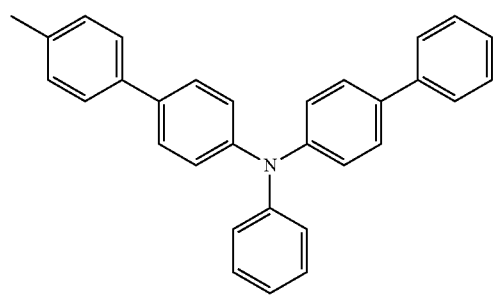 [SMILES: Cc1ccc(-c2ccc(N(c3ccccc3)c3ccc(-c4ccccc4)cc3)cc2)cc1]
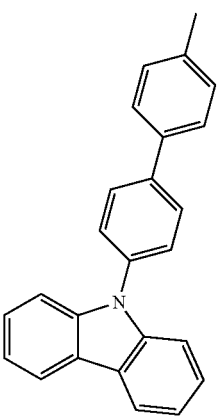
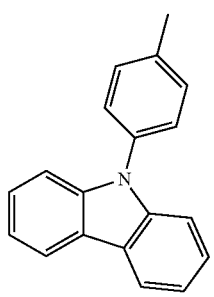 [SMILES: Cc1ccc(-n2c3ccccc3c3ccccc32)cc1]

Most preferably, wherein R1, R2, R3 are independently selected from hydrogen, methyl, phenyl, Ar1-Ar2 independently represent phenyl, naphthyl or biphenyl.

The applications of above said organic electronic materials in the fields of OLED, organic solar cells, organic thin film transistors or organic photoreceptors.

As mentioned above, the specific embodiments in the invention are as follows, but not limited to the structures as below:

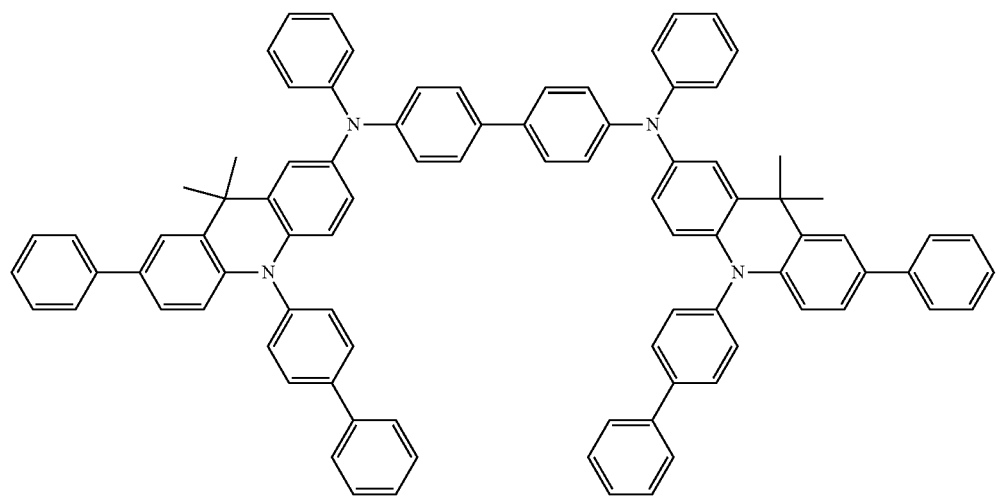

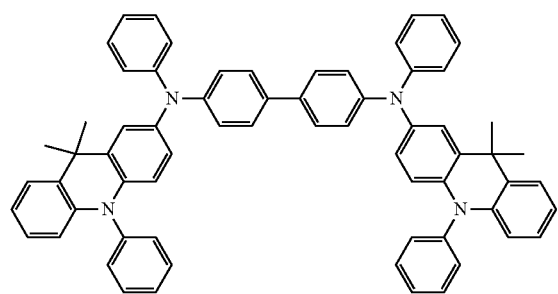

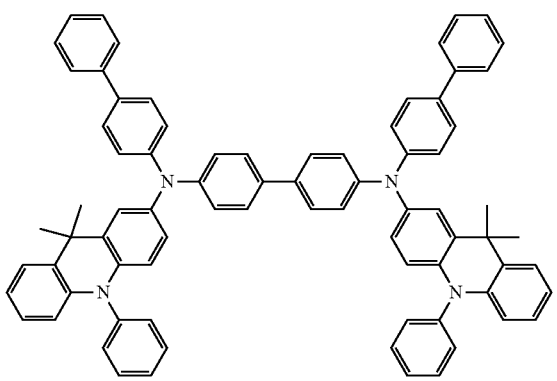

-continued
4
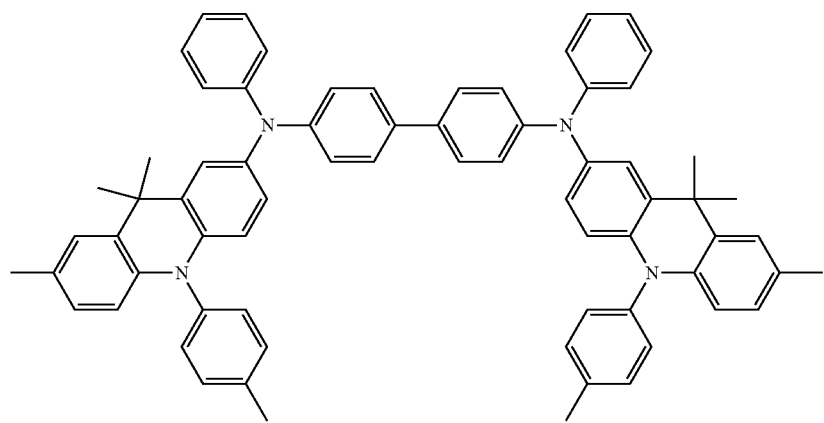
5
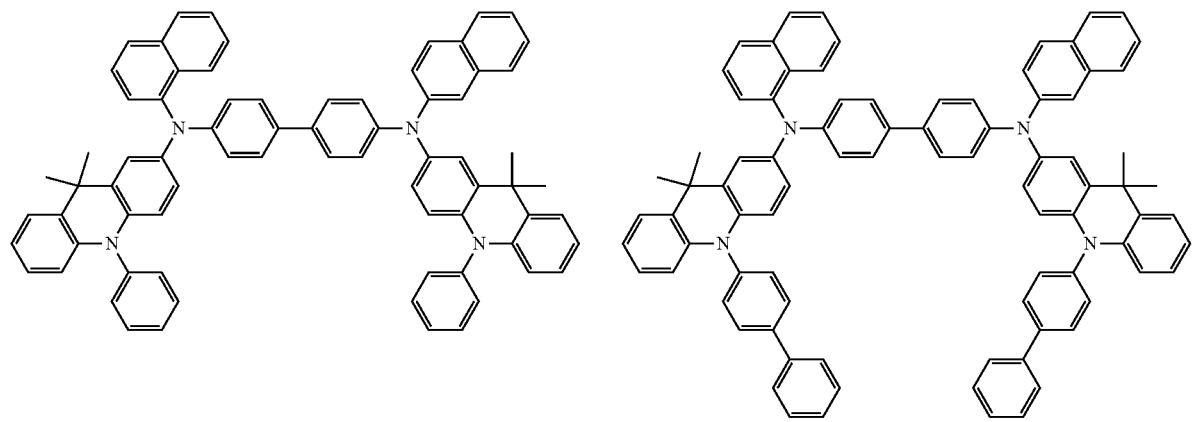
6
7
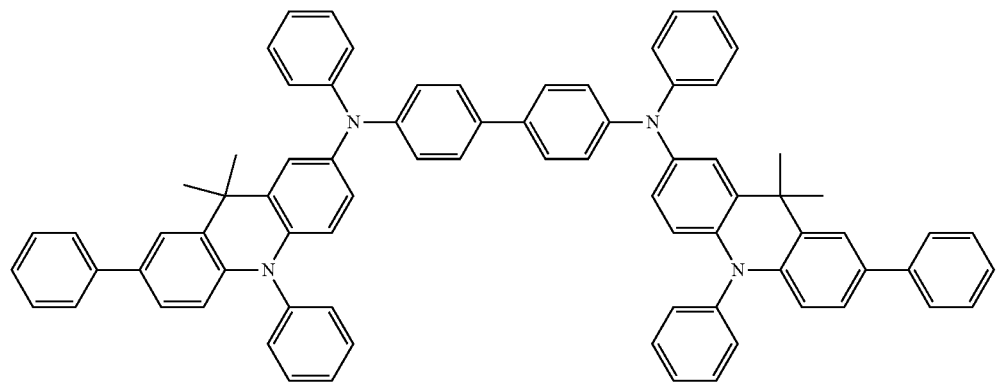
8
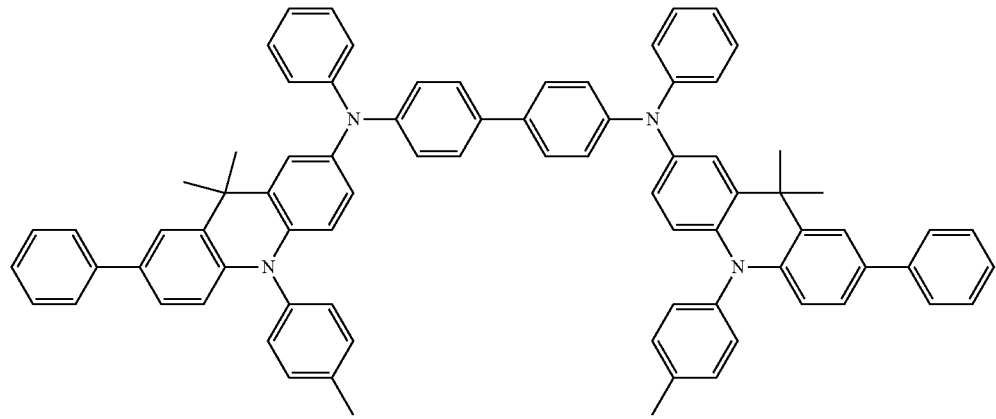

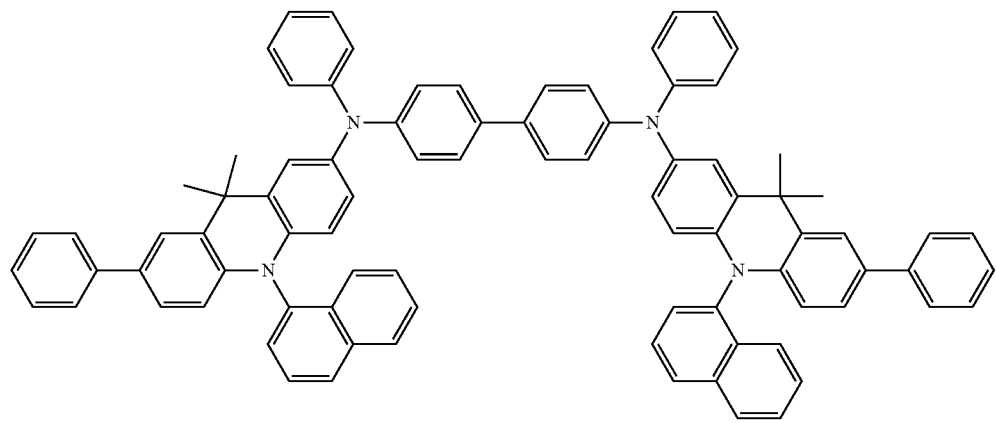
9
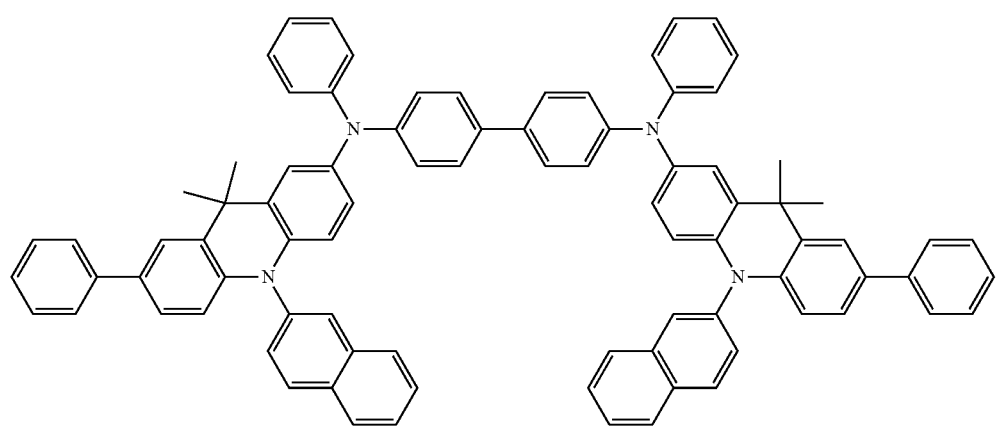
10
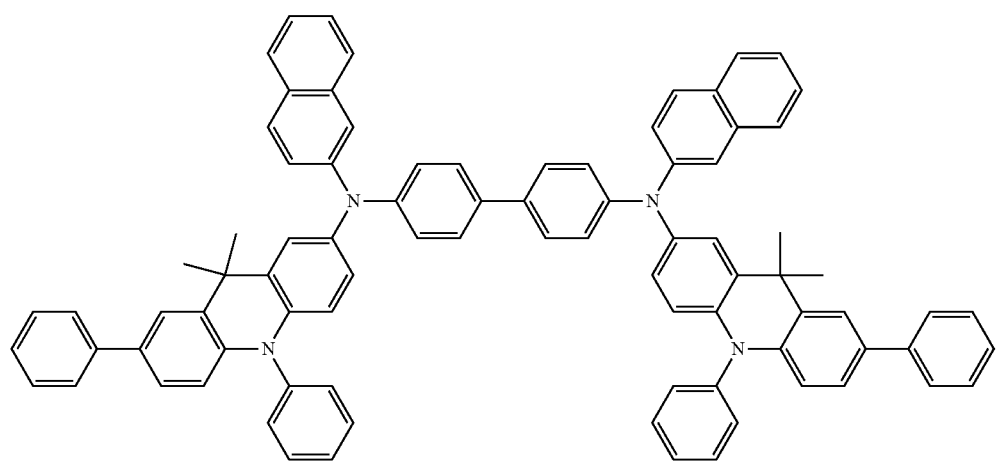
11

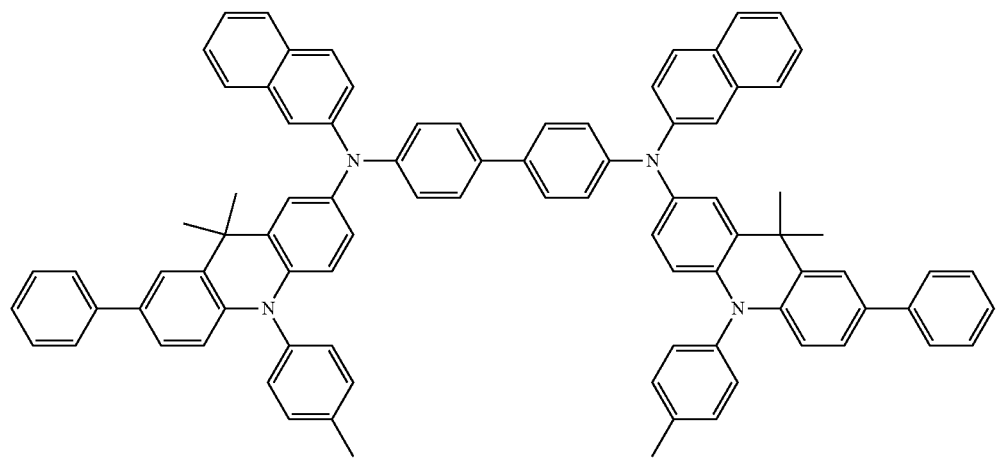
12
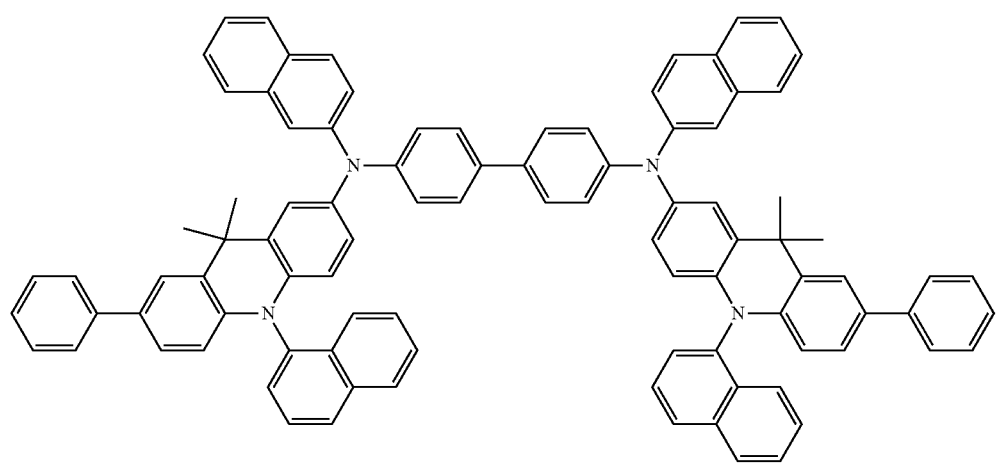
13
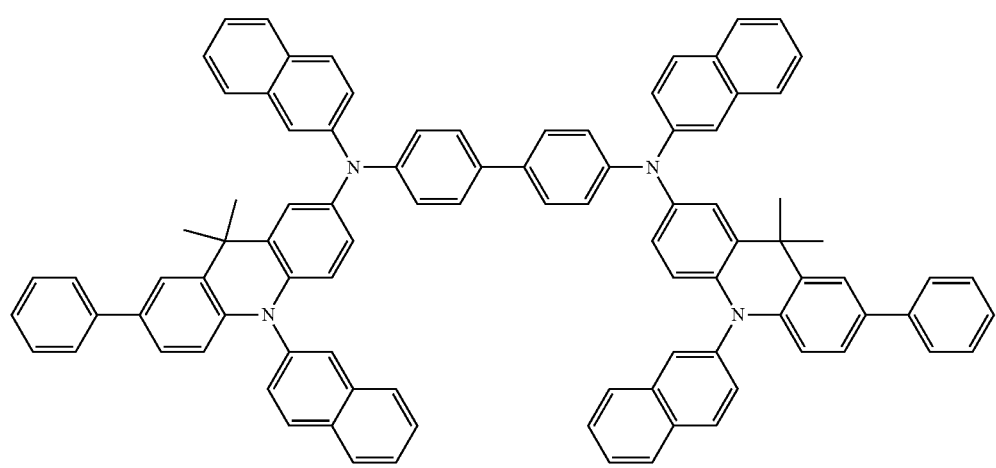
14

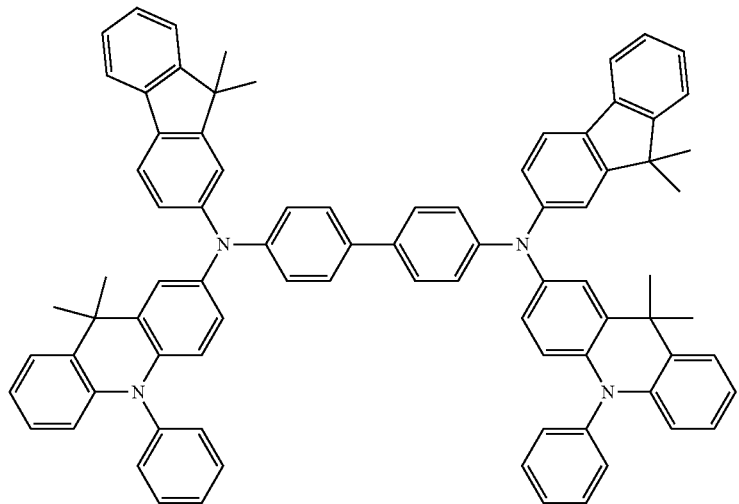
15
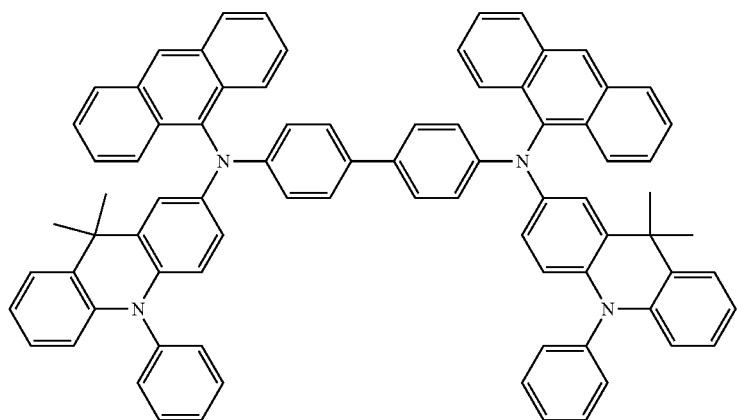
16
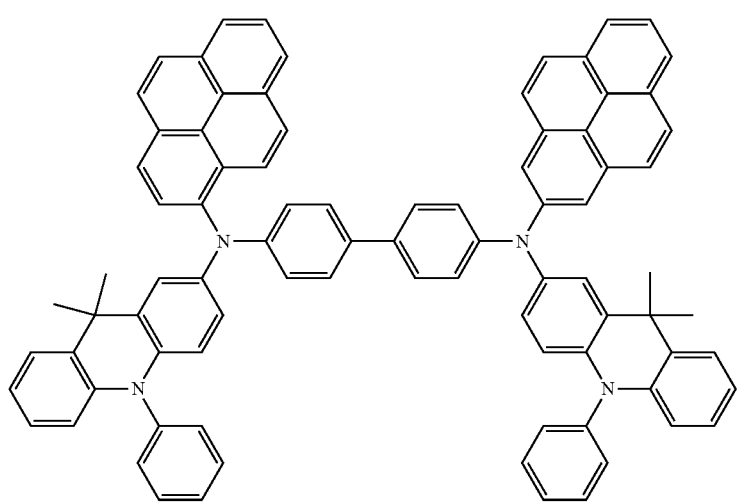
17

18
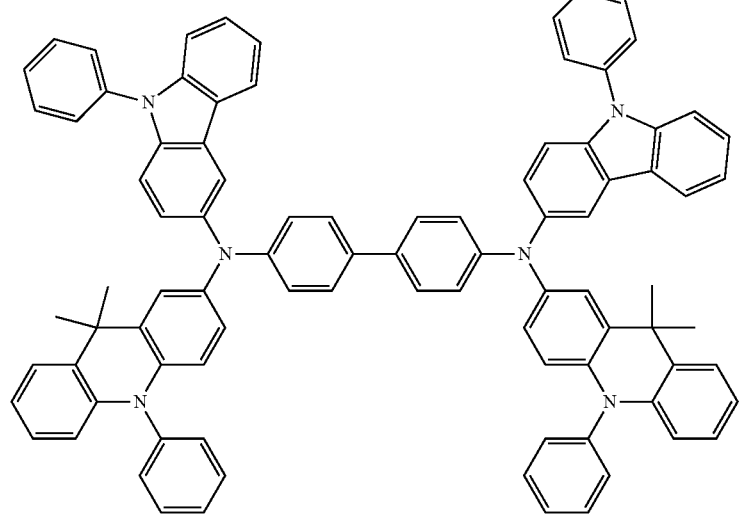
19
20
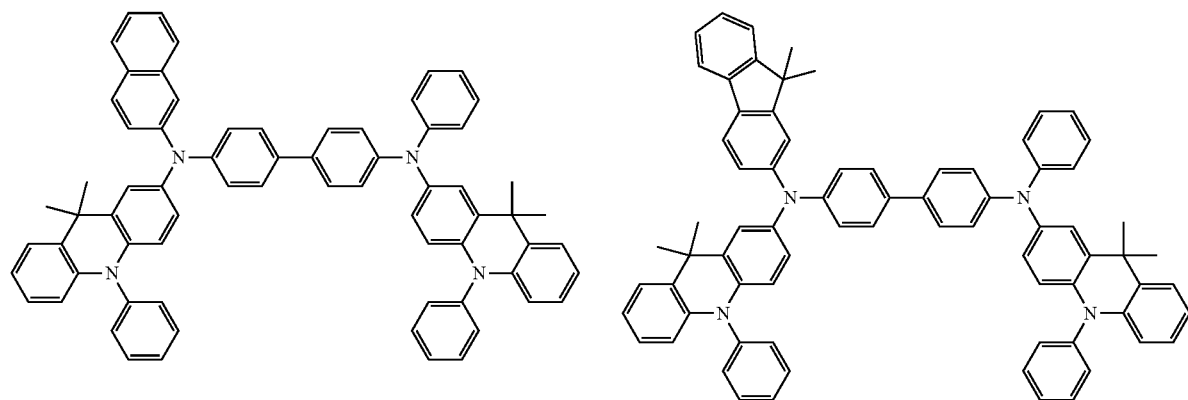
21
22
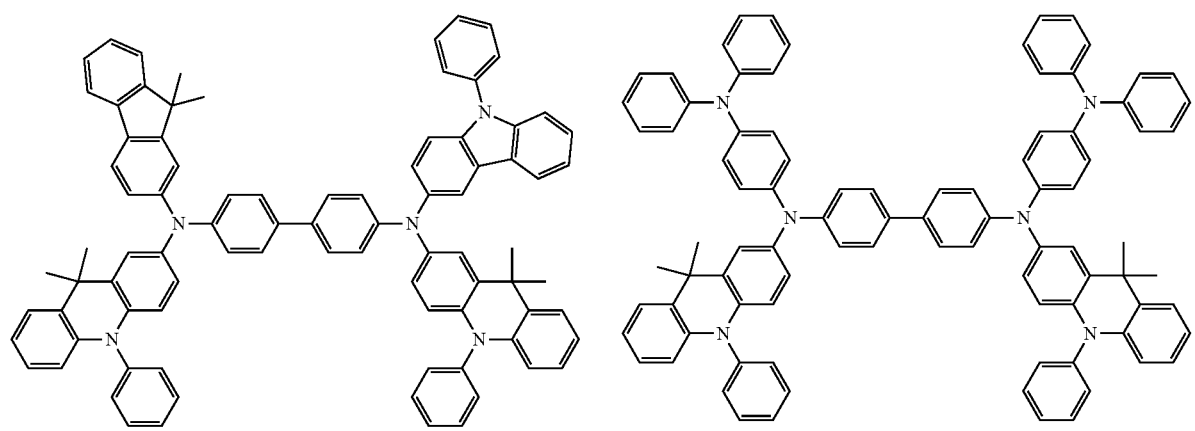

-continued
23
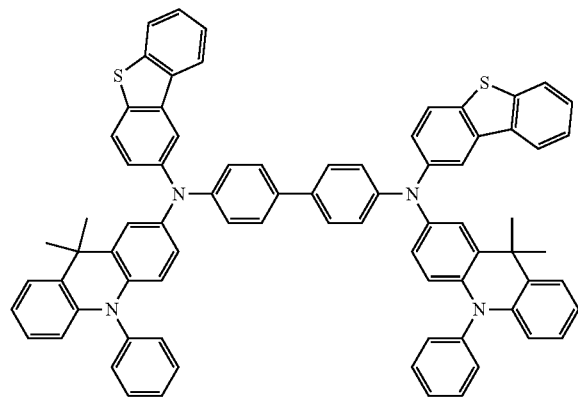
24
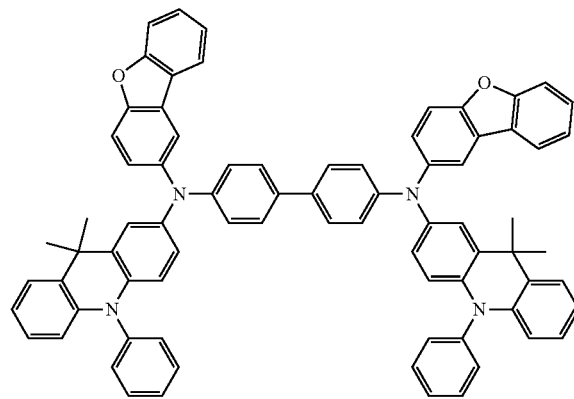
25
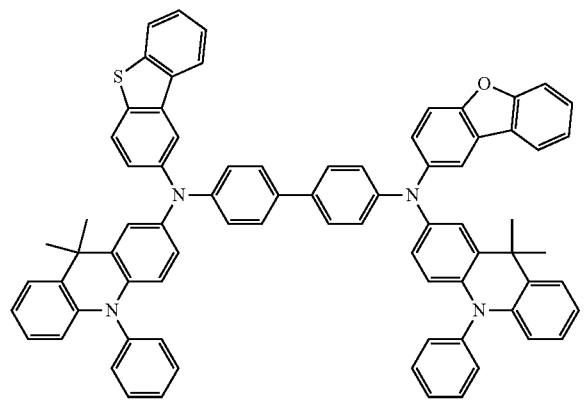
26
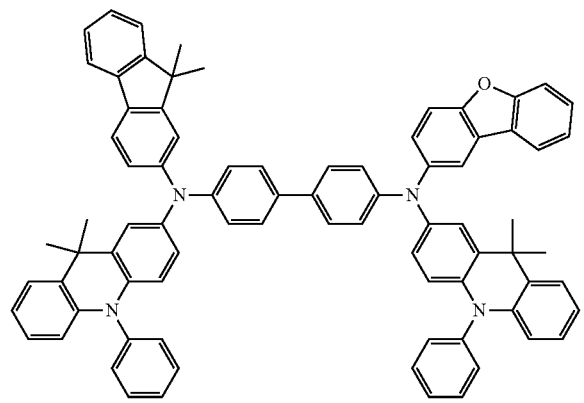
27
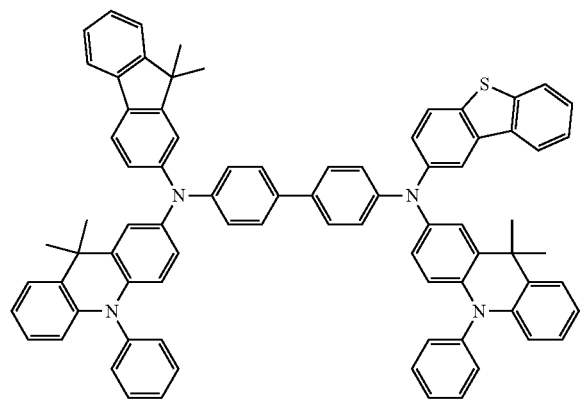
28
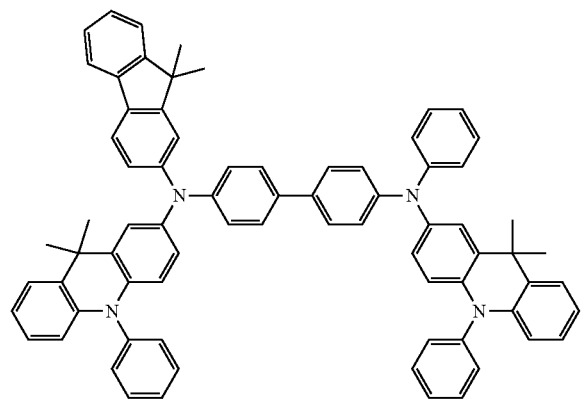

-continued
29
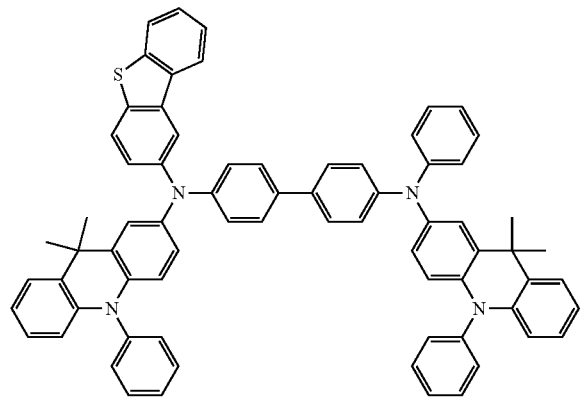
30
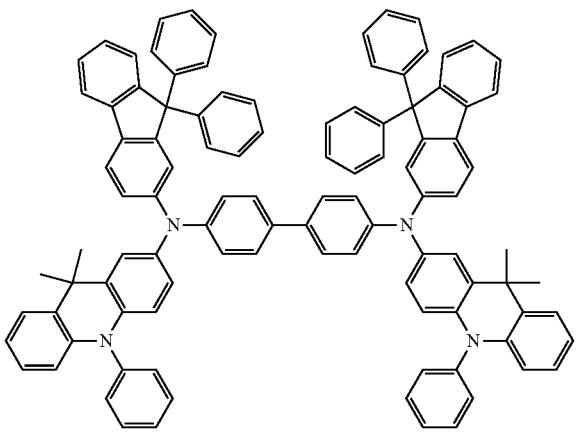
31
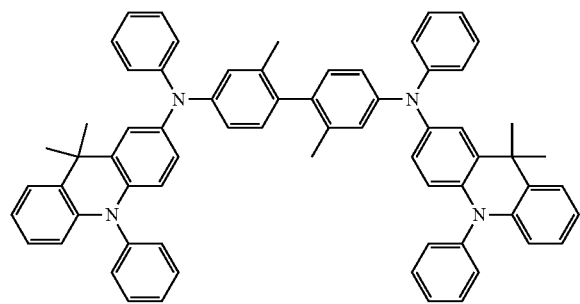
32
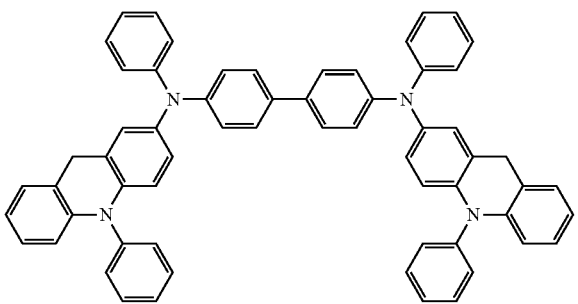
33
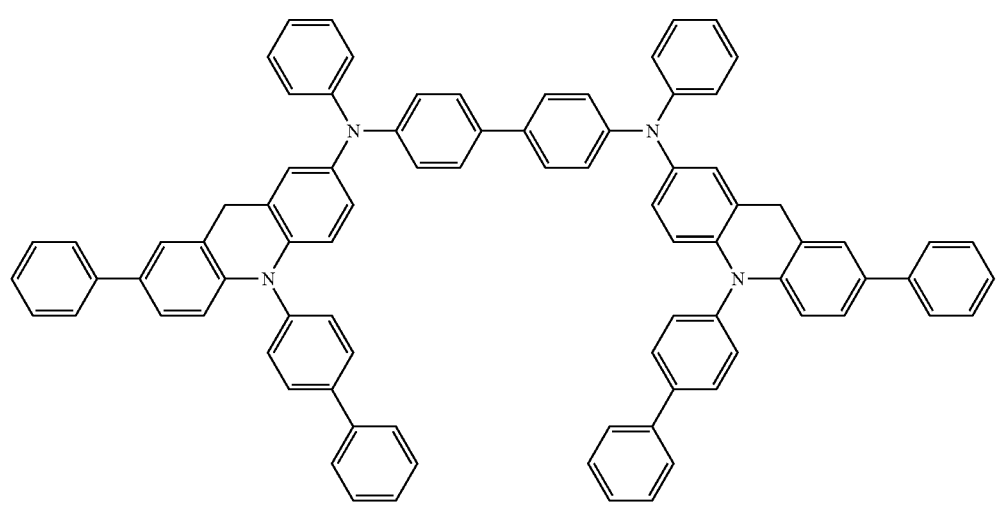

34
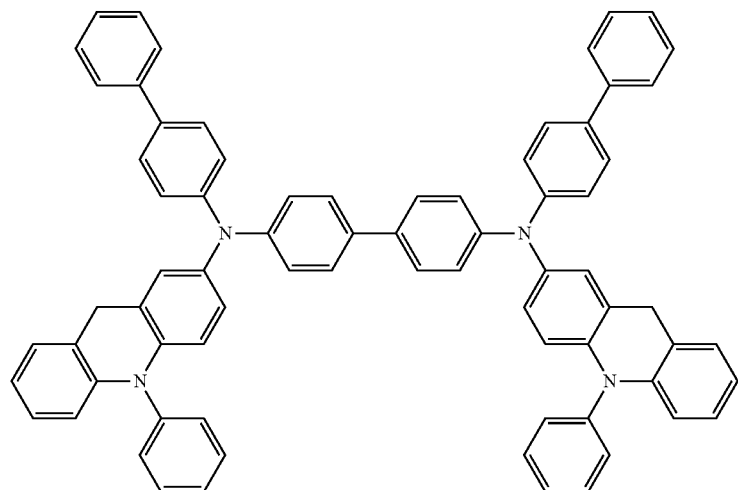
35
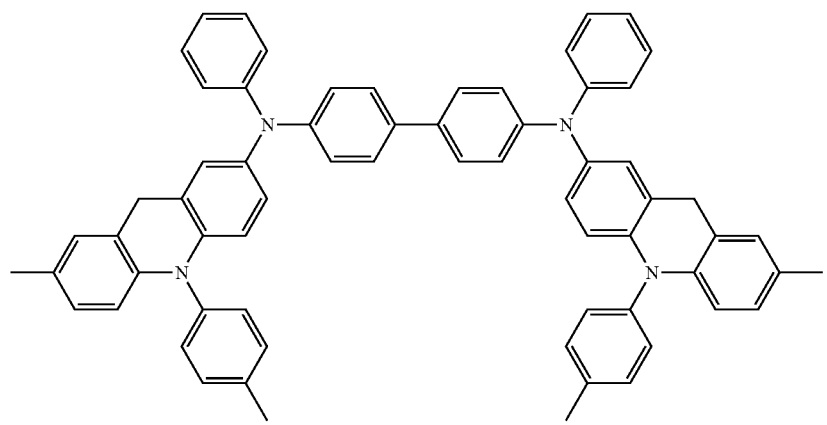
36
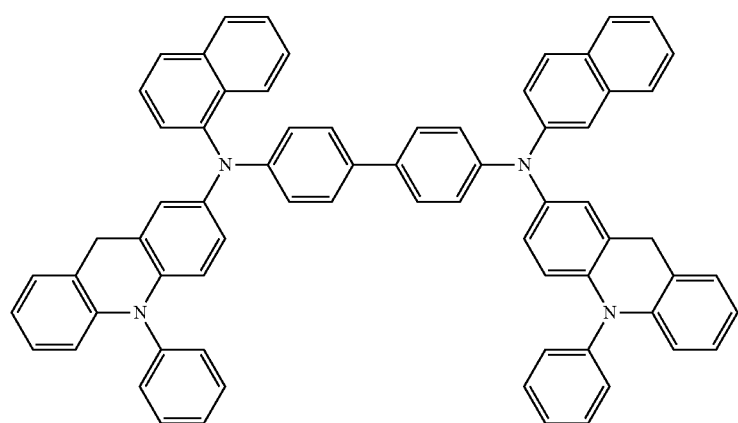

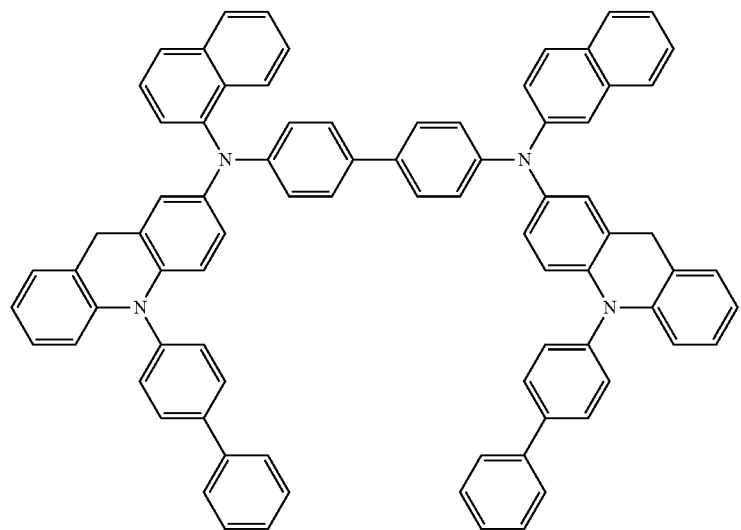
37
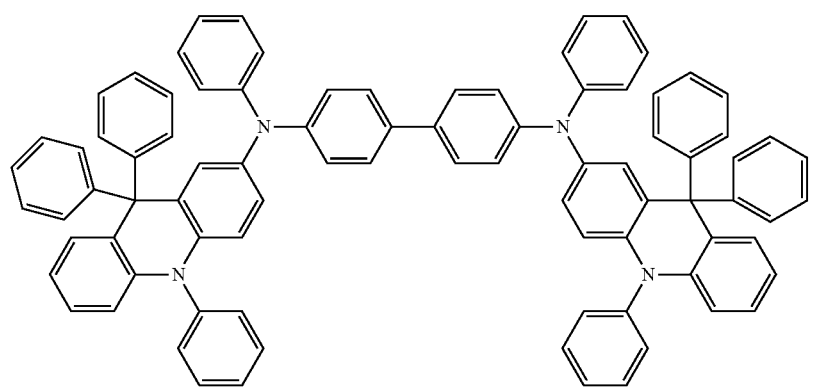
38
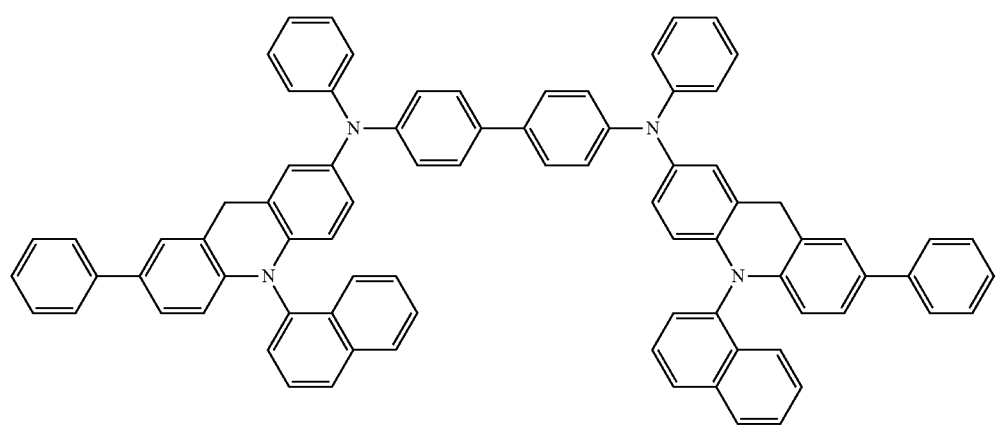
39

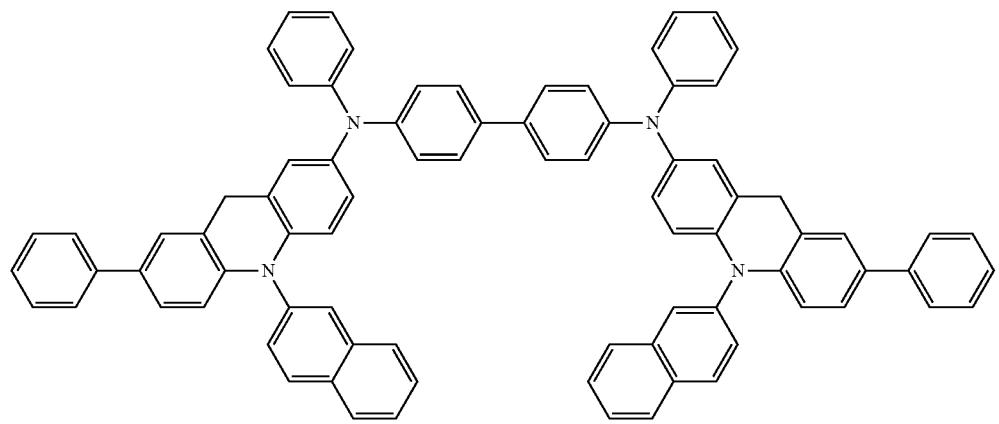

40

The OLED produced by the material in the present invention comprises an anode, a cathode, and a layer or multiple layers of organic layers. The said organic layer includes at least one layer of said organic electronic material with the structural formula I. The said organic layer includes the hole injection layer, hole transport layer, light emitting layer, hole blocking layer, electron transport layer and electron injection layer, and in particular, not all organic layers are necessary according to the demands.

The OLED in the present invention at least includes one layer of organic material with the structural formula I between the anode and light emitting layer, which can exist as a separate layer, or as one kind of mixed component.

The OLED in the present invention at least include one layer of organic material with the structural formula I as the hole transport layer or hole injection layer. It can exist in a layer separately or can be mixed with other chemical components.

The OLED in the present invention may include one light emitting layer, which at least contains one compound with the structural formula I. The emitting region of the light emitting layer is within the range of 380-740 nm, covering the entire white light region. Preferably the range is within 380-550 nm, and more preferably, emit blue light within the range of 440-490 nm.

The compound with the formula I is used as undoped single light emitting layer or doped light emitting layer.

The said doped light emitting layer comprises host material and guest material. The compound with the formula I can be host material or guest material as needed. Two compounds containing the structural formula I are the host material and guest material respectively.

When the compound with structural formula (I) is used as the host material, its concentration is 20-99.9% of the whole light emitting layer in weight, preferably 80-99%, more preferably 90-99%. When the compound with structural formula (I) is used as the guest material, its concentration is 0.01-80% of the whole light emitting layer in weight, preferably 1-20%, more preferably 1-10%.

The materials of the hole transport layer and hole injection layer in the present invention should have good hole transport performance, which can effectively transport the holes from the anode to the organic light emitting layer. In addition to the materials with the structural formula I, the materials used can include small molecule and polymer organic materials, including but not limited to tri-aromatic amine compounds, benzidine compounds, thiazole compounds, oxazole compounds, imidazole compounds, fluorene compound, phthalocyanine compounds, hexanitrile hexaazatriphenylene, 2,3,5,6-tetrafluoro-7,7',8,8'-tetracyanoanthraquinodimethane dimethyl-p-benzoquinone (F4-TCNQ), polyvinyl carbazole, polythiophene, polyethylene, polyethylene sulfonic acid.

The organic light emitting layer contains, in addition to compounds in the present invention, the following but not limited to the following compounds: naphthalene compounds, pyrene compounds, fluorene compounds, phenanthrene compounds, chrysene compounds, fluoranthene compounds, anthracene compounds, dibenzanthracene compounds, perylene compound, bi-aryl vinyl compounds, triphenylamine vinyl compounds, amine compounds, benzimidazole compounds, furan compounds and organic metal chelate compounds.

The organic electron transport material of the organic electronic devices in the present invention should have good electron-transport performance, which can efficiently transfer electrons from the cathode to the light emitting layer. These materials can select the following compounds, but not limited to oxa oxazole, thiazoles, triazole compounds, tri-diazoxide compounds, tri-aza benzene compounds, quinoxaline compounds, dinitrogen anthracene compounds, silicon-containing heterocyclic compounds, quinoline compounds, phenanthroline compounds, metal chelates, fluoro-substituted benzene compounds.

One electron injection layer can be added to the organic electronic device of the present invention as required. The electron injection layer may effectively inject the electrons from the cathode into the organic layer, mainly selected from alkali metals or alkali metal compounds, or selected from alkaline earth metals or alkaline earth metal compounds, including but not limited to the following: lithium, lithium fluoride, lithium oxide, lithium nitride, 8-hydroxyquinoline lithium, cesium, cesium carbonate, 8-hydroxyquinoline cesium, calcium, calcium fluoride, calcium oxide, magnesium, magnesium fluoride, magnesium carbonate, magnesium oxide.

The total thickness of the electron device organic layer in the present invention is 1-1000 nm, preferably 1-500 nm, and more preferably 50-300 nm.

Each layer of the OLED in the present invention can be produced by evaporation or spin-coating, or ink jet printing. The evaporation used in the present invention is vacuum evaporation, with the vacuum degree less than $10^{-5}$ bar, preferably less than $10^{-6}$ bar.

Experimental results show that, the organic light-emitting material with structural formula (I) has a good thermal stability, high hole mobility, high light-emitting efficiency, high light-emitting purity. The OLEDs made from this organic light-emitting material will have advantages of good light-emitting efficiency, excellent color purity and long life.

DETAILED DESCRIPTIONS OF THE PREFERRED EMBODIMENTS

Figure 1:
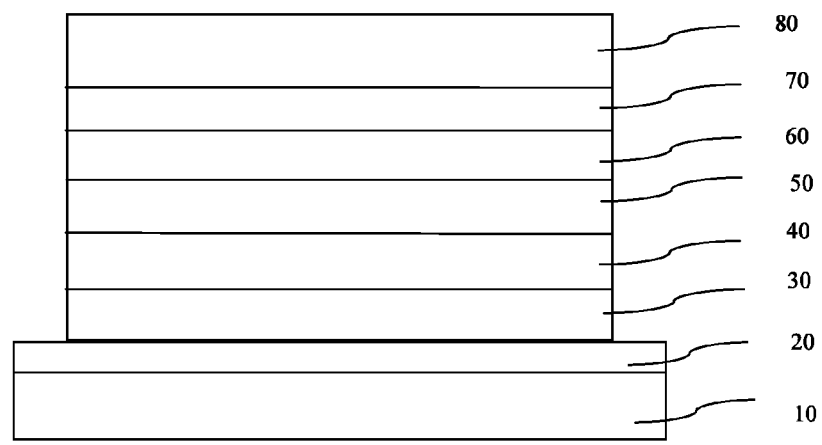
FIG. 1 is a structural chart of the device, of which, 10 denotes a glass substrate, 20 denotes an anode, 30 denotes hole injection layer, 40 denotes hole transport layer, 50 denotes light emitting layer, 60 denotes electron transport layer, 70 denotes electron injection layer, 80 denotes cathode.

In the following, the present invention is described in details by combining the following examples.

Embodiment 1
Synthesis of Compound 2

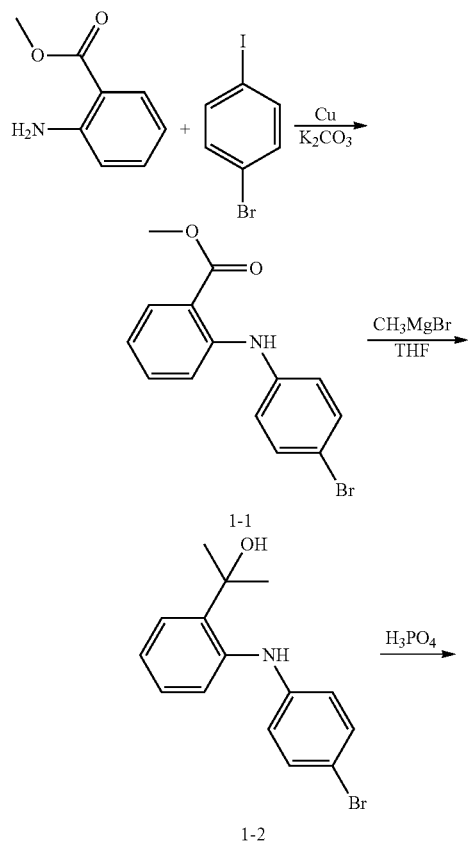

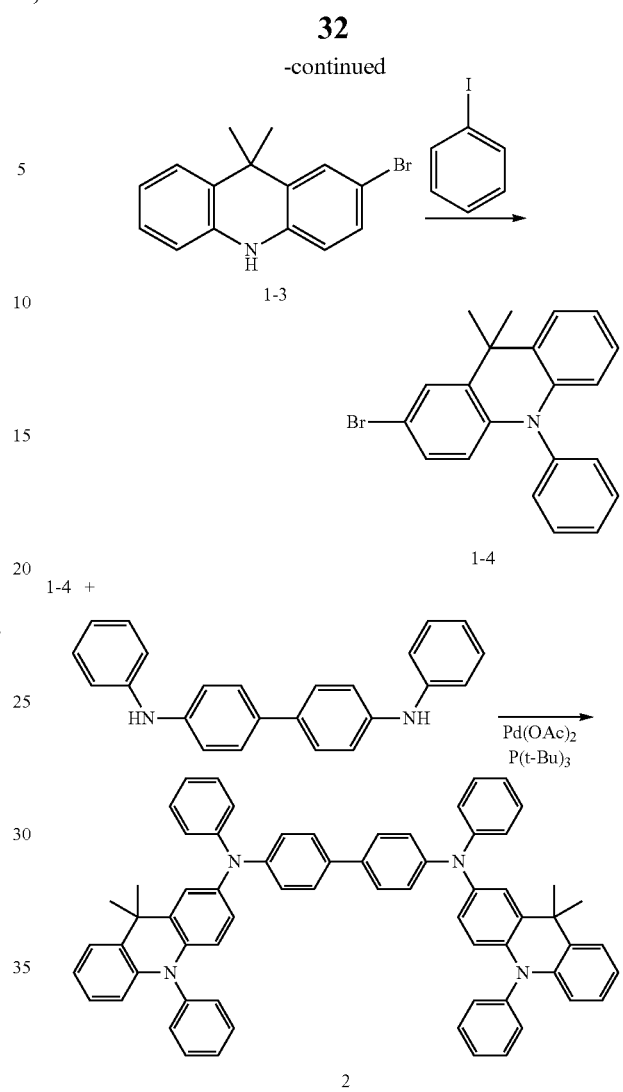

Synthesis of Intermediate 1-1

In a 1 L three-necked flask, add the compound methyl anthranilate and bromoiodobenzene, cuprous iodide, potassium carbonate, o-dichlorobenzene; with the protection of nitrogen, heat them to 180° C. for 24 h, cooled to 100° C., then filter. Remove the solvent in the filtrate by pressure reduction, and then separate it to get compound 1-1 through column chromatography, with a yield 92%, HPLC purity 96%.

Synthesis of Intermediate 1-2

In a 1 L three-necked flask, add the compound 1-1 and tetrahydrofuran. With the protection of nitrogen, cool to 0° C., then dropwise add the methulmagnesium bromide, slowly heat to the room temperature, react overnight, and then add 1N hydrochloric acid solution, extract with ethyl acetate, dry, concentrate it, and then separate to get compound 1-2 through column chromatography, with a yield 83%, HPLC purity 93%.

Synthesis of Intermediate 1-3

In a 1 L three-necked flask, add the compound 1-2, phosphoric acid, stir to react completely, then add them to the water to filter. The filter cake is washed twice with methanol solution, to get the intermediate 1-3, with a yield 80% and HPLC content 90%.

Synthesis of Intermediate 1-4

In a 1 L three-necked flask, add compound 1-3 and iodobenzene, potassium tert-butoxide, tri-tert-butylphosphine, xylene; with the protection of nitrogen, heat them to 120° C. for 24 hours, cool down to room temperature, filter. Remove the solvent in the filtrate by pressure reduction, and then separate it to get compound 1-4 through column chromatography.

Synthesis of Compound 2

In a 1 L three-necked flask, add compound 1-4 and biphenyl diamine, potassium tert-butoxide, tri-tert-butylphosphine and xylene. With the protection of nitrogen, heat to 120° C. for 24 hours, cool down to 100° C., filter. Remove the solvent in the filtrate by pressure reduction, and then separate it to get compound 2 through column chromatography.

ESI-MS m/z 902.4.

Embodiment 2
Preparation of OLED
Prepare OLED Using the OEL Material in the Invention Firstly, the ITO transparent conductive glass substrate 10 (with the anode 20 above) is subject to washing by detergent solution ethanol, acetone and deionized water, and then treated by oxygen plasma for 30 seconds.

Then, the compound 2 with 10 nm thick is evaporated on ITO as the hole injection layer 30.

Then, the compound NPB is evaporated to form hole transport layer 40 with thickness of 60 nm.

Then, the compound $Alq_3$ with thickness of 50 nm is evaporated on the hole transport layer as the light emitting layer 50.

Then, the $Alq_3$ with thickness of 10 nm is evaporated on light emitting layer as the electron transport layer 60.

Finally, 1 nm Liq is evaporated as the electron injection layer 70 and 100 nm Al as the device cathode 80.

Embodiment 3
Preparation of OLED
Prepare OLED Using the OEL Material in the Invention Firstly, the ITO transparent conductive glass substrate 10 (with the anode 20 above) is subject to washing by detergent solution ethanol, acetone and deionized water, and then treated by oxygen plasma for 30 seconds.

Then, the compound 2 with 10 nm thick is evaporated on ITO as the hole injection layer 30.

Then, the compound NPB is evaporated to form hole transport layer 40 with thickness of 60 nm.

Then, the compound $Alq_3$ with thickness of 50 nm is evaporated on the hole transport layer as the light emitting layer 50.

Then, the $Alq_3$ with thickness of 10 nm is evaporated on light emitting layer as the electron transport layer 60.

Finally, 1 nm Liq is evaporated as the electron injection layer 70 and 100 nm Al as the device cathode 80.

Embodiment 4
Preparation of OLED
Prepare OLED Using the OEL Material in the Invention Firstly, the ITO transparent conductive glass substrate 10 (with the anode 20 above) is subject to washing by detergent solution ethanol, acetone and deionized water, and then treated by oxygen plasma for 30 seconds.

Then, the compound 2 with 10 nm thick is evaporated on ITO as the hole injection layer 30.

Then, the compound NPB is evaporated to form hole transport layer 40 with thickness of 60 nm.

Then, the compound $Alq_3$ with thickness of 50 nm is evaporated on the hole transport layer as the light emitting layer 50.

Then, the $Alq_3$ with thickness of 10 nm is evaporated on light emitting layer as the electron transport layer 60.

Finally, 1 nm Liq is evaporated as the electron injection layer 70 and 100 nm Al as the device cathode 80.

Embodiment 5
Preparation of OLED
Prepare OLED Using the OEL Material in the Invention Firstly, the ITO transparent conductive glass substrate 10 (with the anode 20 above) is subject to washing by detergent solution ethanol, acetone and deionized water, and then treated by oxygen plasma for 30 seconds.

Then, the compound 2 with 10 nm thick is evaporated on ITO as the hole injection layer 30.

Then, the compound NPB is evaporated to form hole transport layer 40 with thickness of 60 nm.

Then, the compound $Alq_3$ with thickness of 50 nm is evaporated on the hole transport layer as the light emitting layer 50.

Then, the $Alq_3$ with thickness of 10 nm is evaporated on light emitting layer as the electron transport layer 60.

Finally, 1 nm Liq is evaporated as the electron injection layer 70 and 100 nm Al as the device cathode 80.

Comparative Example 1
Preparation of OLED
Prepare OLED Using the OEL Material in the Invention Firstly, the ITO transparent conductive glass substrate 10 (with the anode 20 above) is subject to washing by detergent solution ethanol, acetone and deionized water, and then treated by oxygen plasma for 30 seconds.

Then, the compound NPB is evaporated on ITO to form hole transport layer 40 with thickness of 60 nm.

Then, the compound $Alq_3$ with thickness of 50 nm is evaporated on the hole transport layer as the light emitting layer 50.

Then, the $Alq_3$ with thickness of 10 nm is evaporated on light emitting layer as the electron transport layer 60.

Finally, 1 nm Liq is evaporated as the electron injection layer 70 and 100 nm Al as the device cathode 80.

The structural form of device

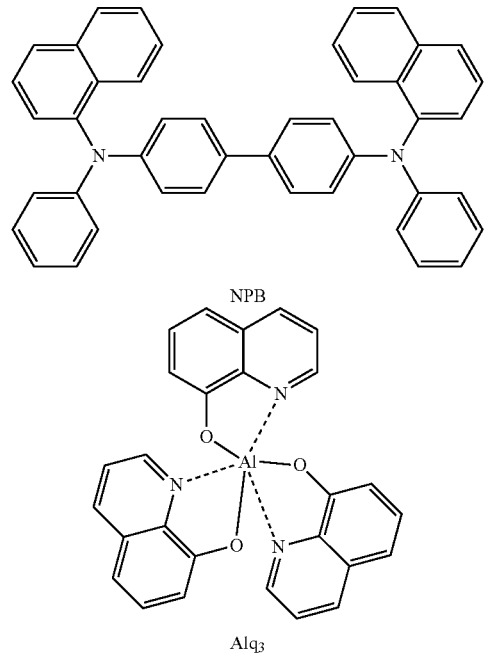

NPB $Alq_3$

Figure 2:
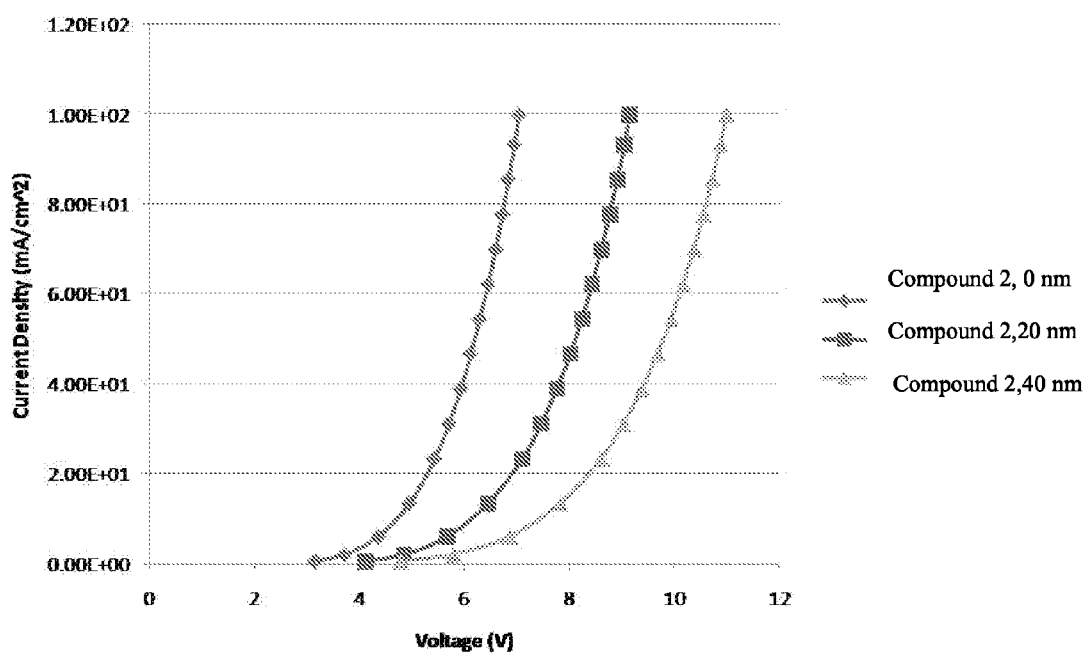
FIG. 2 is the chart of device current density and voltage in Embodiment 3, Embodiment 5 and Comparative Example 1
Figure 3:
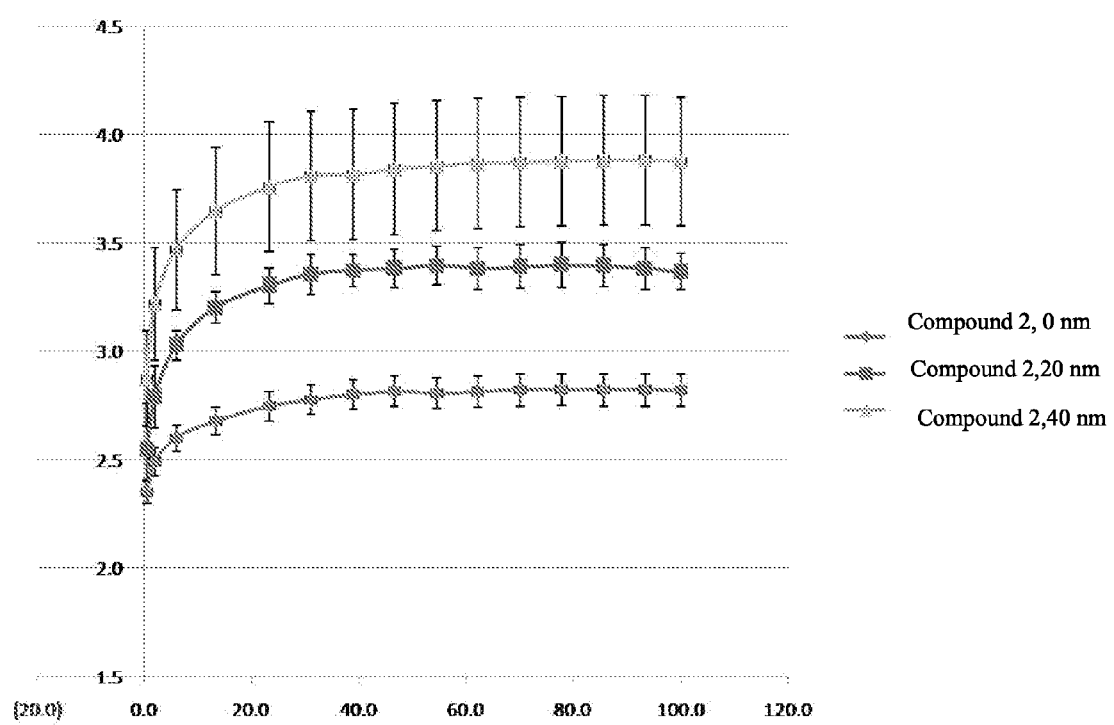
FIG. 3 is the chart of device light-emitting efficiency and current density in Embodiment 3, Embodiment 5 and Comparative Example 1
Figure 4:
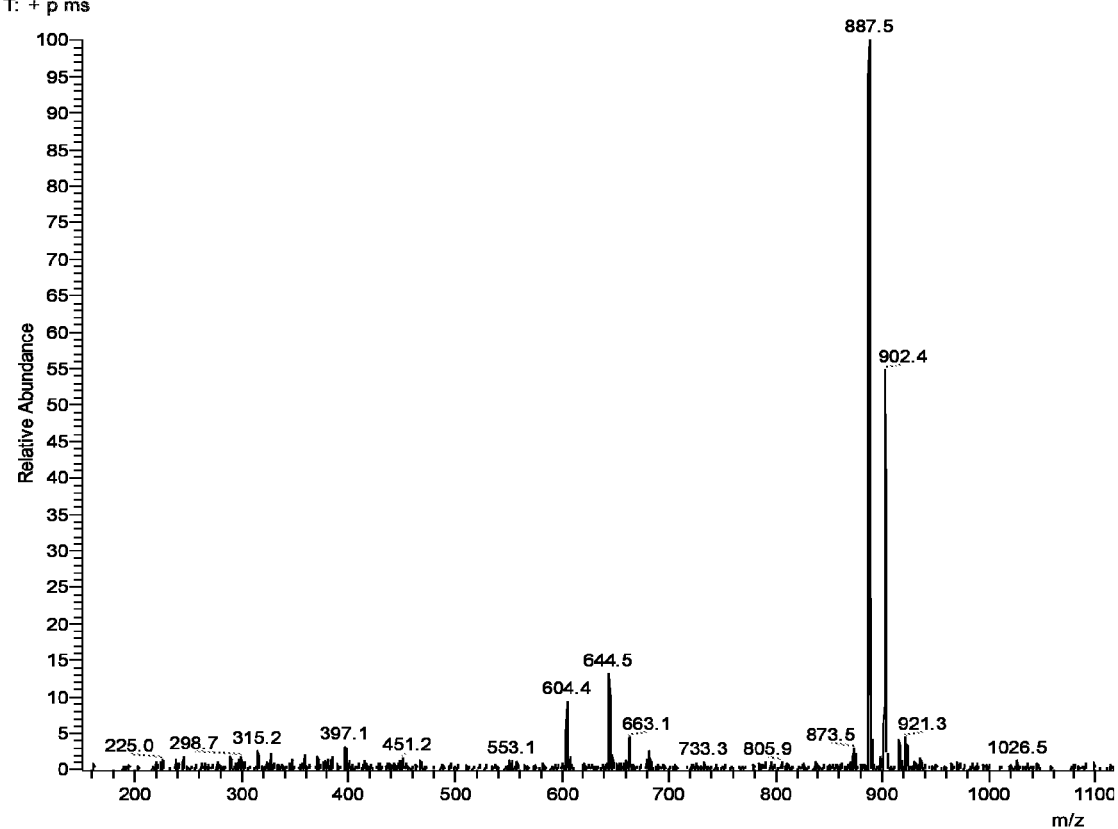
FIG. 4 is the electrospray ionization mass spectrum of compound 2 in Embodiment 1.

The light-emitting data of device are shown in FIGS. 2 and 3.

Table 1 shows the CIE coordinates of device in Embodiments 2-5 in the present invention

| | | $CIE_x, CIE_y$ |
|---|---|---|
| Compound 2, 0 nm | Comparative example 1 | 0.35, 0.53 |
| Compound 2, 10 nm | Embodiment 2 | 0.35, 0.53 |
| Compound 2, 20 nm | Embodiment 3 | 0.33, 0.53 |
| Compound 2, 30 nm | Embodiment 4 | 0.33, 0.53 |
| Compound 2, 40 nm | Embodiment 5 | 0.32, 0.54 |

In Comparative Example 1, in the absence of organic light-emitting material with formula (I) as the hole injection material, the light-emitting efficiency is only 2.7 cd/A; however, after the hole injection material is added, its effect is significantly improved. In Embodiment 5, the organic light-emitting material with formula (I) is used as the hole injection material with 40 nm in thickness, and the light-emitting efficiency is increased by over 37% compared to Embodiment 1, which is up to 3.7 cd/A.

Experimental results show that, the organic light-emitting material with structural formula (I) has a good thermal stability, high hole mobility, high light-emitting efficiency, high light-emitting purity. The OLEDs made from this organic light-emitting material will have advantages of good light-emitting efficiency, excellent color purity and long lifetime.

The invention claimed is:

1. An organic electronic material has the following structural formula (I):

Structural formula I

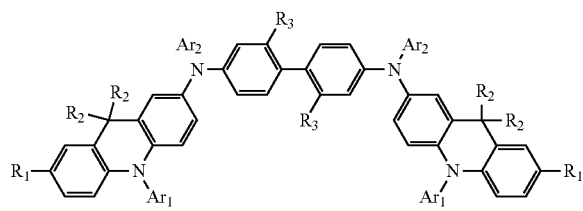

(I)

wherein, $R_1$-$R_3$ independently represent hydrogen, deuterium, halogen, cyano, nitro, C1-C8 alkyl, C1-C8 alkoxy, C6-C30 aryl unsubstituted or substituted by one or more substituent group R, C3-C30 heteroaryl containing one or more heteroatoms unsubstituted or substituted by one or more substituent group R, C2-C8 alkenyl unsubstituted or substituted by one or more substituent group R, C2-C8 alkynyl unsubstituted or substituted by one or more substituent group R, C8-C30 diaryl vinyl unsubstituted or substituted by one or more substituent group R, C8-C30 diaryl ethynyl, trialkyl silicon unsubstituted or substituted by one or more substituent group R, C6-C30 triaryl silicon unsubstituted or substituted by one or more substituent group R, C6-C30 diaryl phosphonoso unsubstituted or substituted by one or more substituent group R, C6-C30 aryl carbonyl unsubstituted or substituted by one or more substituent group R, C6-C30 aryl sulfenyl unsubstituted or substituted by one or more substituent group R, C6-C30 aryl fused ring unsubstituted or substituted by one or more substituent group R, C6-C30 substituted or unsubstituted heteroatom-containing aryl fused ring, C6-C30 carbazolyl unsubstituted or substituted by one or more substituent group R, C6-C30 diaryl amine unsubstituted or substituted by one or more substituent group R, or a spiral structure formed between two $R_2$ groups, and the said heteroatoms are B, O, S, N, and Se;

wherein $Ar_1$-$Ar_2$ represent independently C6-C30 aryl containing one or more substituent group R, aryl fused ring unsubstituted or substituted by one or more substituent group R, C6-C30 carbazolyl unsubstituted or substituted by one or more substituent group R, or C6-C30 tri-aromatic amine unsubstituted or substituted by one or more substituent group R; and wherein, R represents independently alkyl, five-or six-membered ring aryl, alkoxy, deuterium, halogen, cyano, nitro, or amino.

2. The organic electronic material according to claim 1, wherein:

$R_1$-$R_3$ are independently selected from hydrogen, halo, C1-C8 alkyl, C6-C30 phenyl group unsubstituted or substituted by one or more substituent group R, diaryl amine unsubstituted or substituted by one or more substituent group R, C6-C30 aryl fused ring unsubstituted or substituted by one or more substituent group R, C6-C30 carbazolyl unsubstituted or substituted by one or more substituent group R, or two $R_2$ forming a spirofluorene structure;

$Ar_1$-$Ar_2$ represent independently C6-C30 aryl containing one or more substituent group R, aryl fused ring unsubstituted or substituted by one or more substituent group R, C6-C30 carbazolyl unsubstituted or substituted by one or more substituent group R, C6-C30 tri-aromatic amine unsubstituted or substituted by one or more substituent group R; and R independently represents an alkyl group, a five- or six-membered ring of aryl, alkoxy, or halogen.

3. The organic electronic material according to claim 2, wherein:

$R_1$-$R_3$ are independently selected from hydrogen, C1-C8 alkyl group, one or more C1-C3 alkyl, C1-C3 alkoxy, aryl-substituted or unsubstituted phenyl, one or more C1-C3 alkyl, C1-C3 alkoxy, aryl-substituted or unsubstituted naphthyl, one or more C1-C3 alkyl, C1-C3 alkoxy, aryl-substituted or unsubstituted carbazolyl or a spiral structure is formed between two $R_2$ groups.

4. The organic electronic material according to claim 3, wherein:

$R_1$, $R_2$ are independently selected from hydrogen, methyl, ethyl, propyl, isopropyl, butyl, t-butyl, n-pentyl, isopentyl, n-hexyl, isohexyl, cyclohexyl, n-octyl, isooctyl, C1-C3 alkyl substituted or unsubstituted phenyl, C1-C3 alkoxy substituted or unsubstituted phenyl, naphthyl or a spiral structure is formed between two $R_2$ groups, one or more methyl, phenyl substituted or unsubstituted diaryl amine, one or more methyl, phenyl substituted or unsubstituted carbazolyl; and $R_3$ is independently selected from hydrogen, C1-C8 alkyl, C1-C3 substituted or unsubstituted phenyl.

5. The organic electronic material according to claim 4, wherein:

$R_1$, $R_2$ are independently selected from hydrogen, methyl, ethyl, propyl, isopropyl, butyl, t-butyl, n-pentyl, isopentyl, n-hexyl, isohexyl, cyclohexyl, n-octyl, iso-octyl, phenyl, tolyl; and $R_3$ is independently selected from hydrogen, C1-C3 alkyl, C1-C3 alkyl substituted or unsubstituted phenyl.

6. The organic electronic material according to claim 5, wherein:

$R_3$ is hydrogen, methyl, phynyl;

$R_1$, $R_2$ are independently selected from hydrogen, methyl, t-butyl, phenyl;

R1, R2 are independently selected to form a spiro structure between hydrogen, methyl, t-butyl, phenyl or a spiral structure is formed between two $R_2$ groups; and $Ar_1$-$Ar_2$ are independently expressed as any one of the groups in the table below

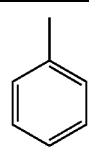

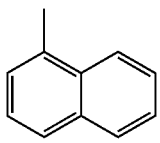

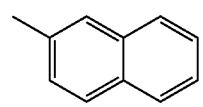

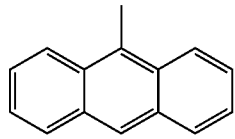

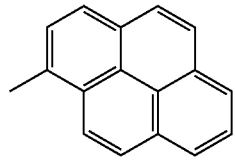 [SMILES: Cc1ccc2ccc3cccc4ccc1c2c34]

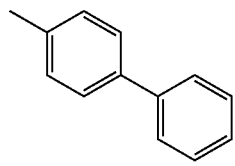

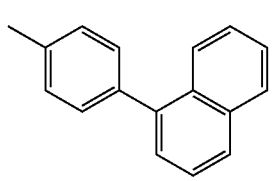 [SMILES: Cc1ccc(-c2cccc3ccccc23)cc1]

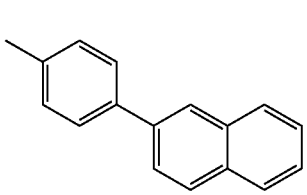 [SMILES: Cc1ccc(-c2ccc3ccccc3c2)cc1]

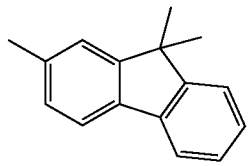 [SMILES: Cc1ccc2c(c1)C(C)(C)c1ccccc1-2]

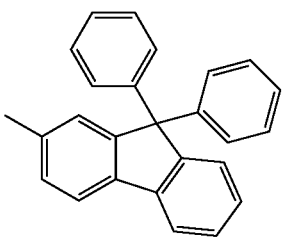 [SMILES: Cc1ccc2c(c1)C(c1ccccc1)(c1ccccc1)c1ccccc1-2]

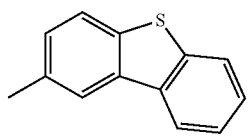

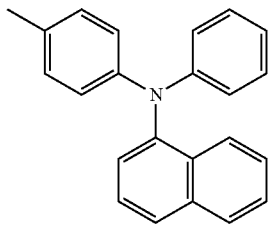 [SMILES: Cc1ccc(N(c2ccccc2)c2cccc3ccccc23)cc1]
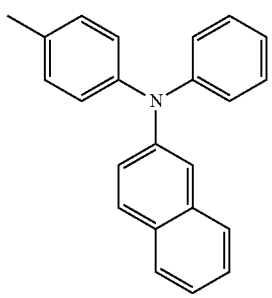 [SMILES: Cc1ccc(N(c2ccccc2)c2ccc3ccccc3c2)cc1]
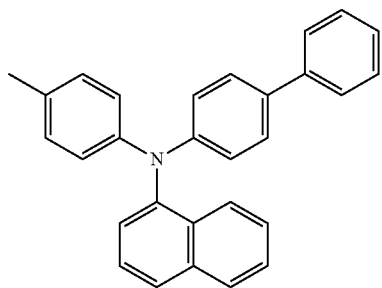 [SMILES: Cc1ccc(N(c2ccc(-c3ccccc3)cc2)c2cccc3ccccc23)cc1]
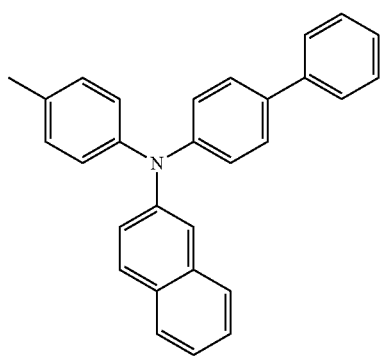 [SMILES: Cc1ccc(N(c2ccc(-c3ccccc3)cc2)c2ccc3ccccc3c2)cc1]
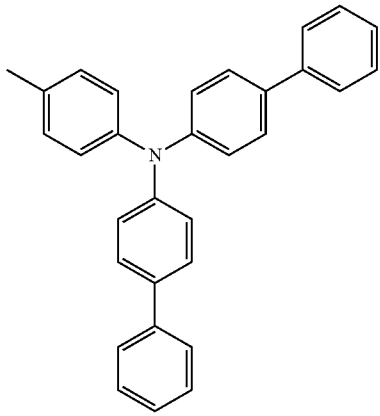 [SMILES: Cc1ccc(N(c2ccc(-c3ccccc3)cc2)c2ccc(-c3ccccc3)cc2)cc1]
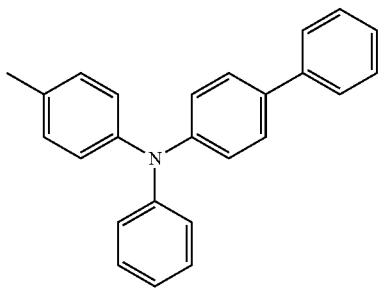 [SMILES: Cc1ccc(N(c2ccccc2)c2ccc(-c3ccccc3)cc2)cc1]
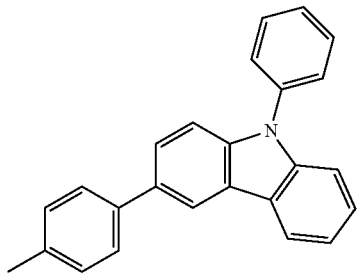 [SMILES: Cc1ccc(-c2ccc3c(c2)c2ccccc2n3-c2ccccc2)cc1]
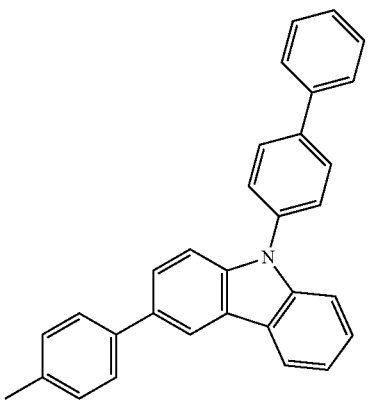 [SMILES: Cc1ccc(-c2ccc3c(c2)c2ccccc2n3-c2ccc(-c3ccccc3)cc2)cc1]

-continued
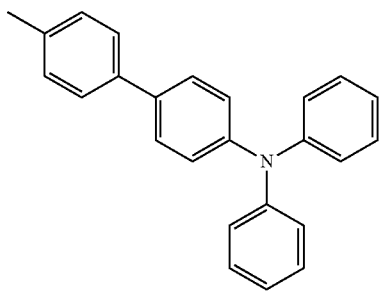 [SMILES: Cc1ccc(-c2ccc(N(c3ccccc3)c3ccccc3)cc2)cc1]
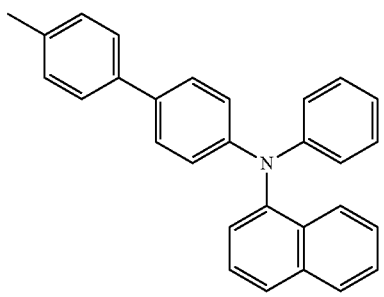 [SMILES: Cc1ccc(-c2ccc(N(c3ccccc3)c3cccc4ccccc34)cc2)cc1]
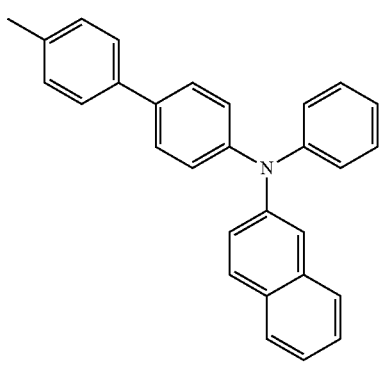 [SMILES: Cc1ccc(-c2ccc(N(c3ccccc3)c3ccc4ccccc4c3)cc2)cc1]
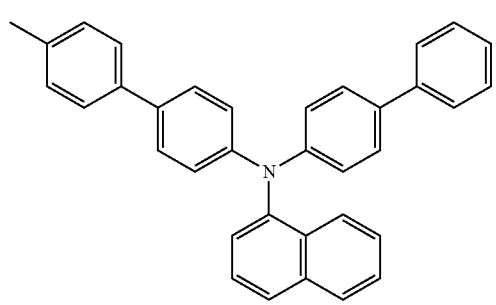 [SMILES: Cc1ccc(-c2ccc(N(c3ccc(-c4ccccc4)cc3)c3cccc4ccccc34)cc2)cc1]
-continued
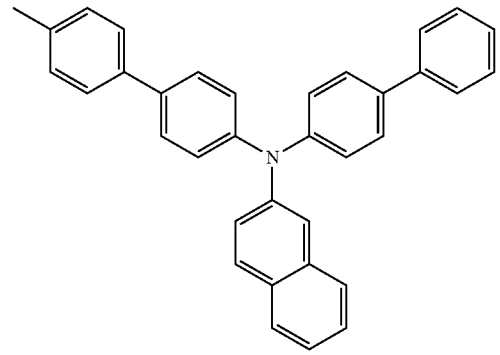 [SMILES: Cc1ccc(-c2ccc(N(c3ccc(-c4ccccc4)cc3)c3ccc4ccccc4c3)cc2)cc1]
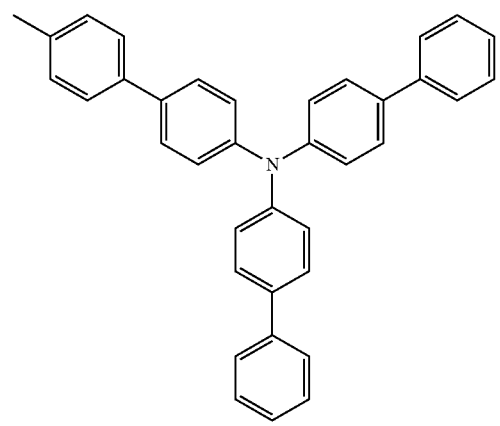 [SMILES: Cc1ccc(-c2ccc(N(c3ccc(-c4ccccc4)cc3)c3ccc(-c4ccccc4)cc3)cc2)cc1]
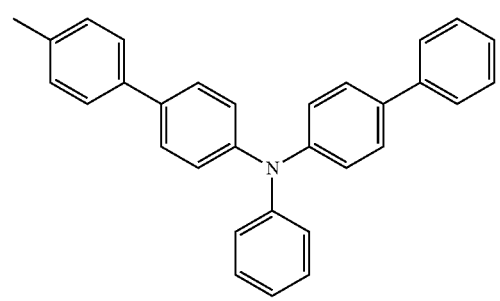 [SMILES: Cc1ccc(-c2ccc(N(c3ccccc3)c3ccc(-c4ccccc4)cc3)cc2)cc1]
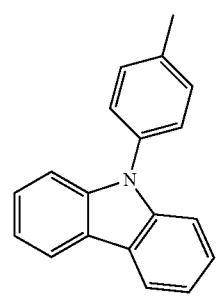 [SMILES: Cc1ccc(-n2c3ccccc3c3ccccc32)cc1]

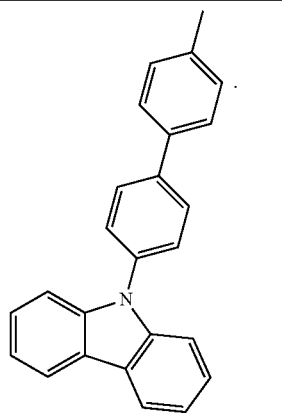
7. The organic electronic material according to claim 5, wherein the compound described in formula I has any of the following structures:
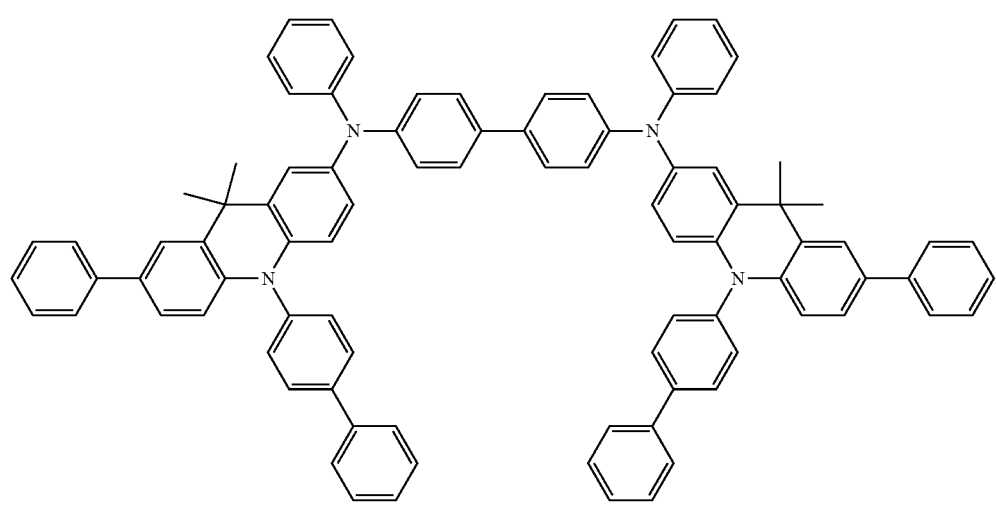
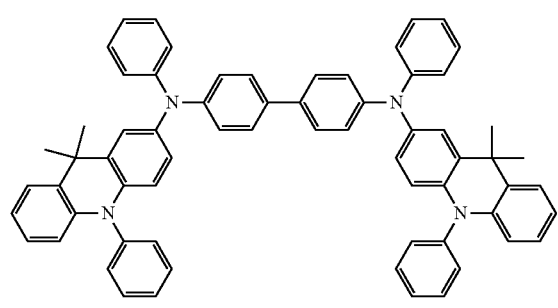
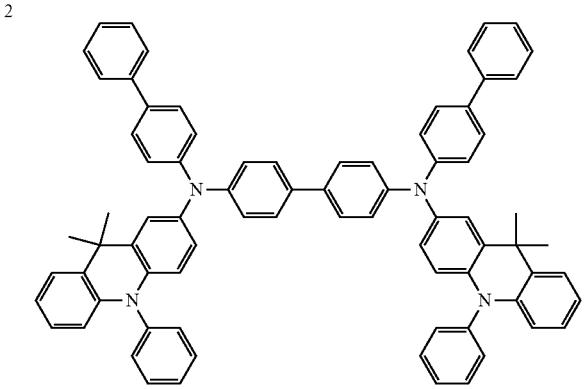

-continued
4
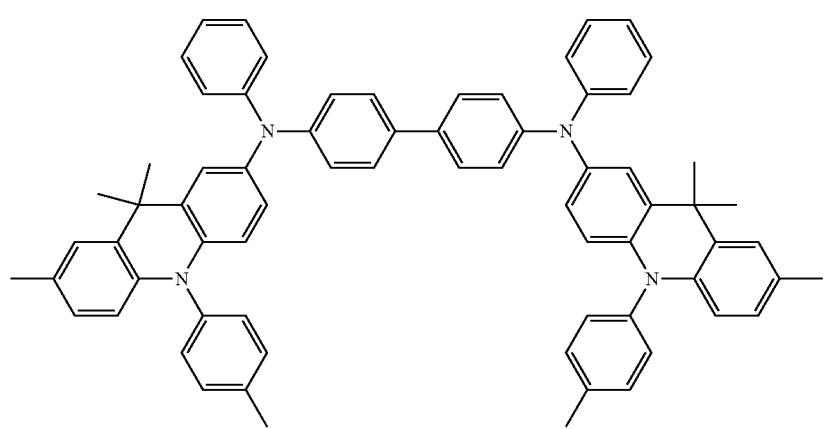
5
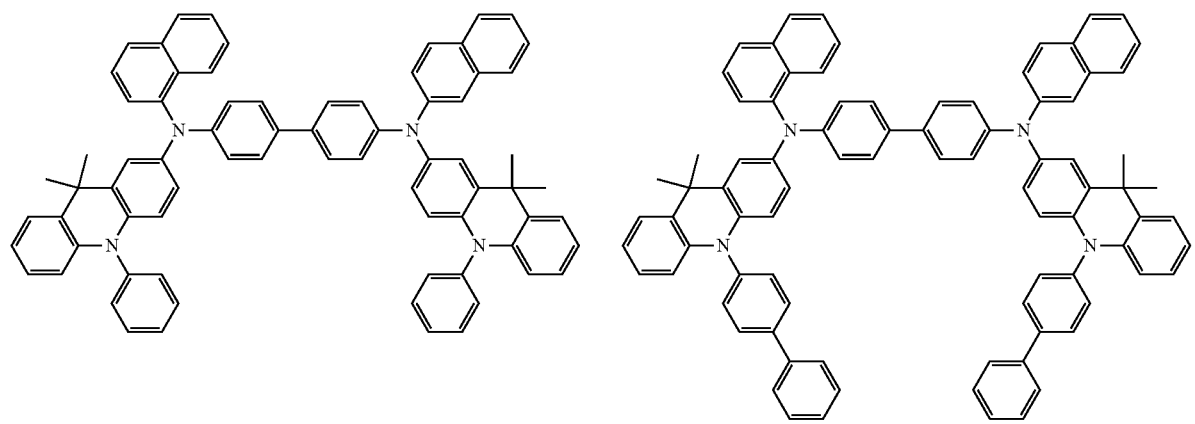
6
7
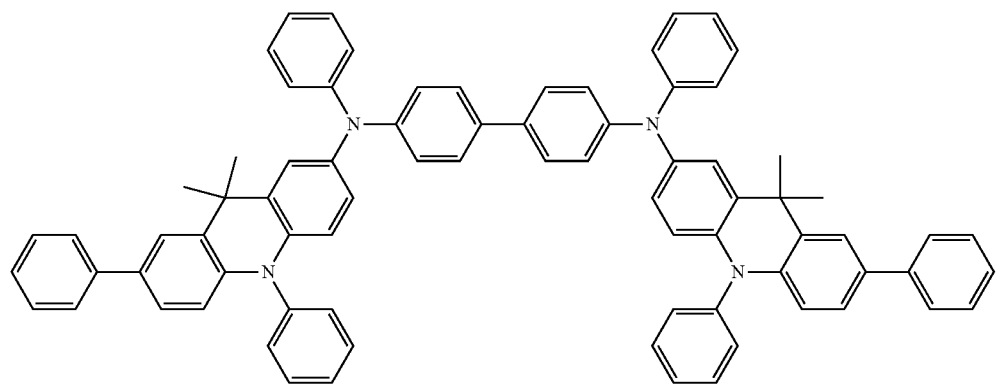
8
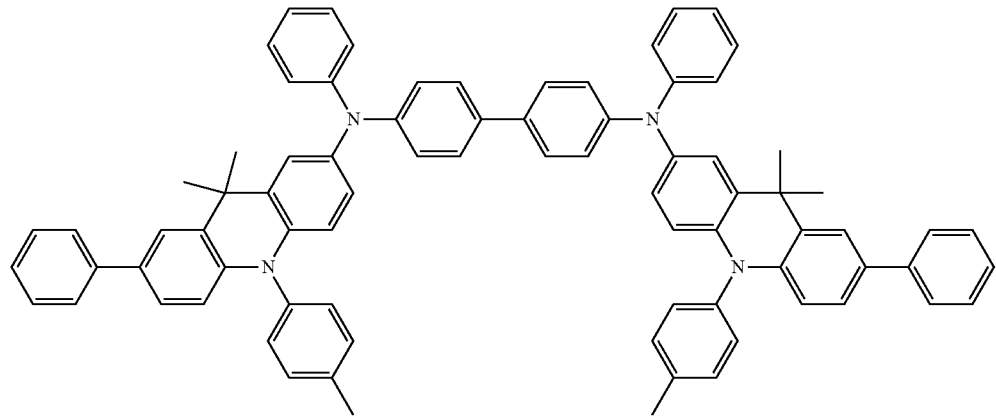

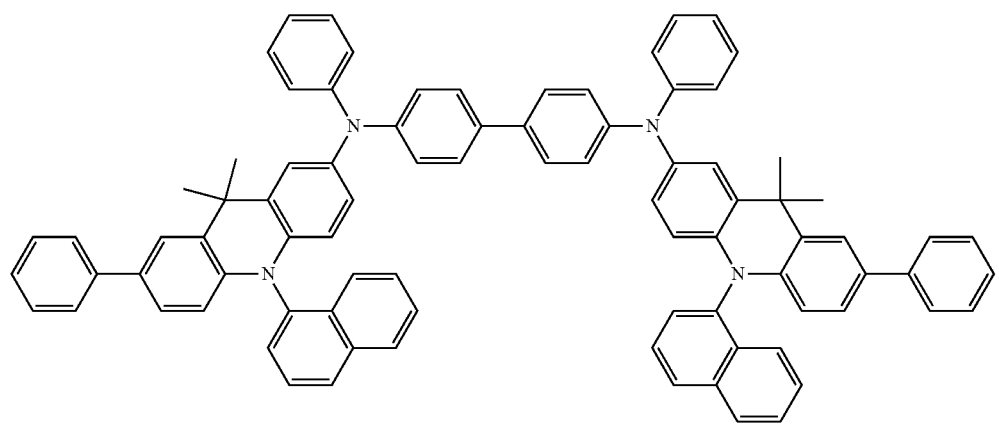
9
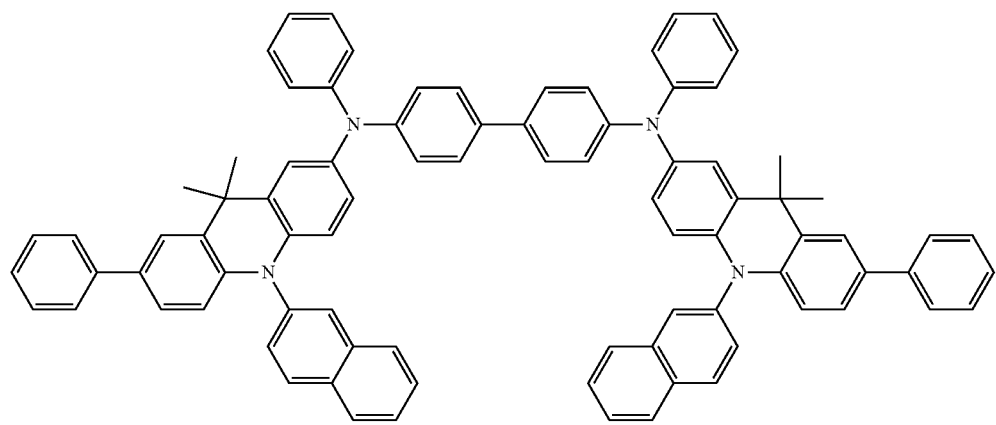
10
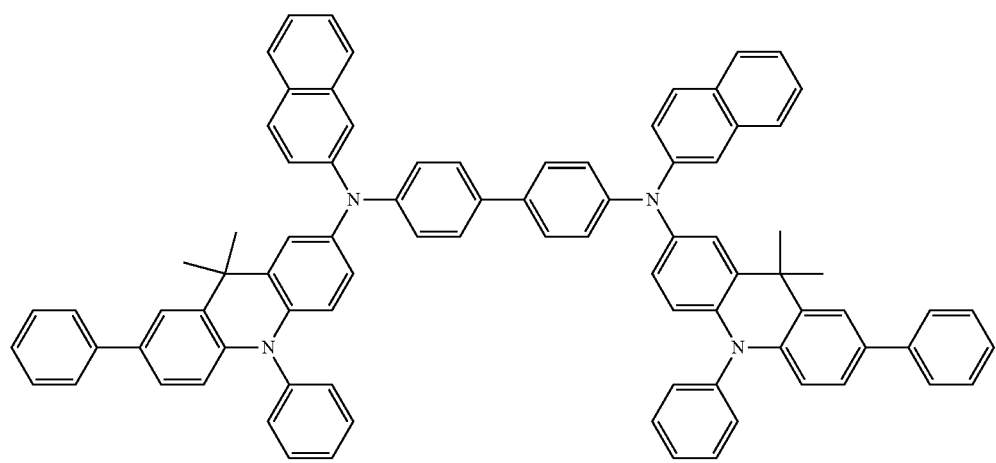
11

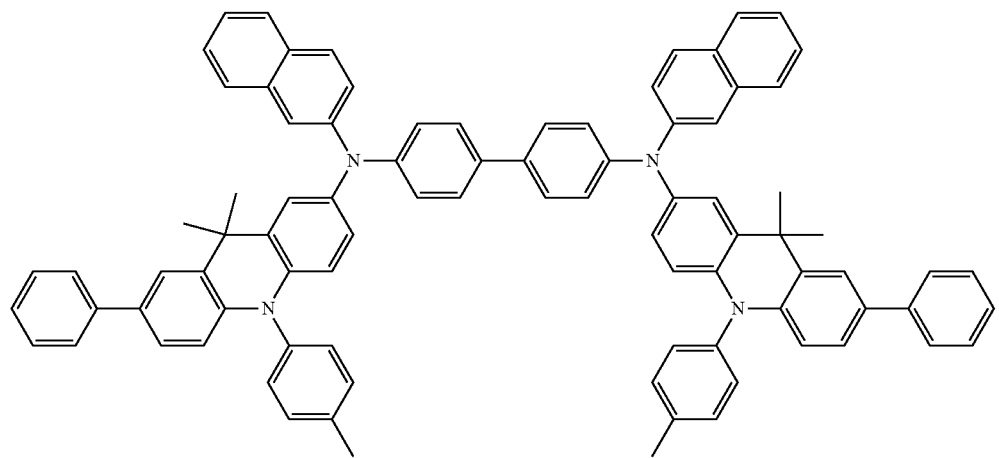
12
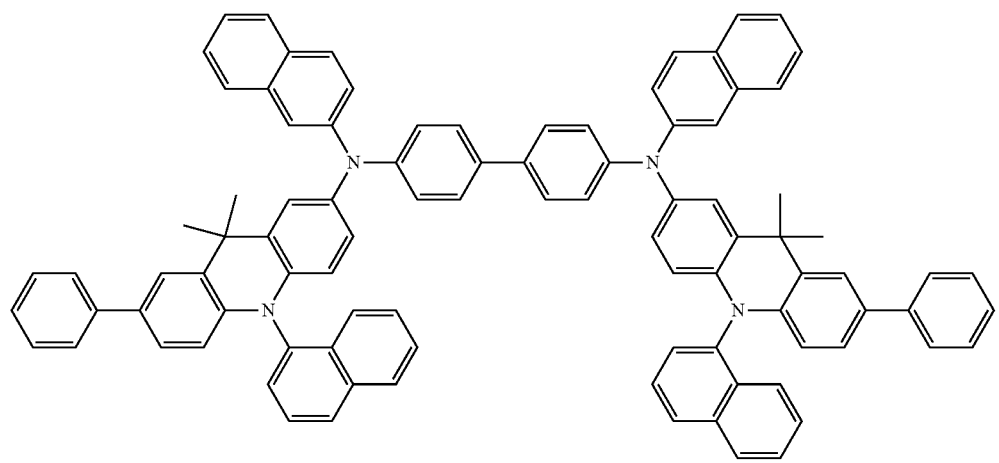
13
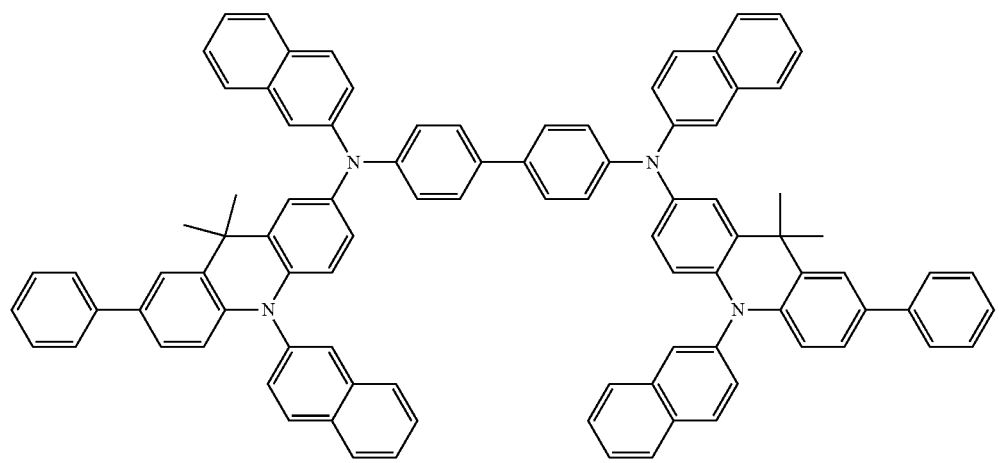
14

-continued
15
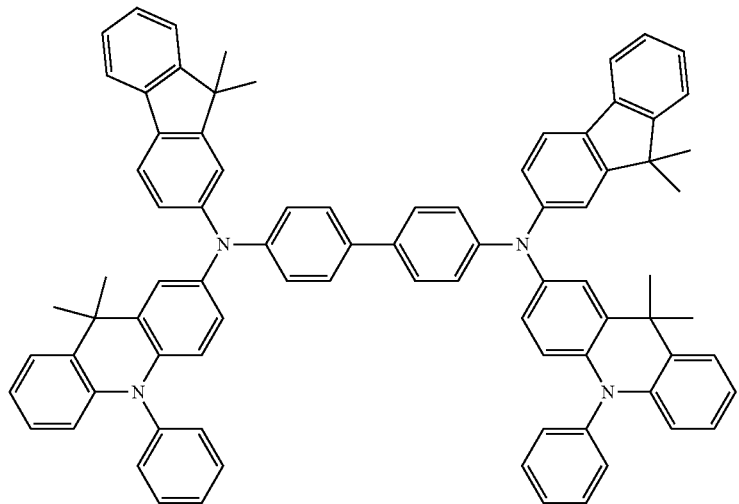
16
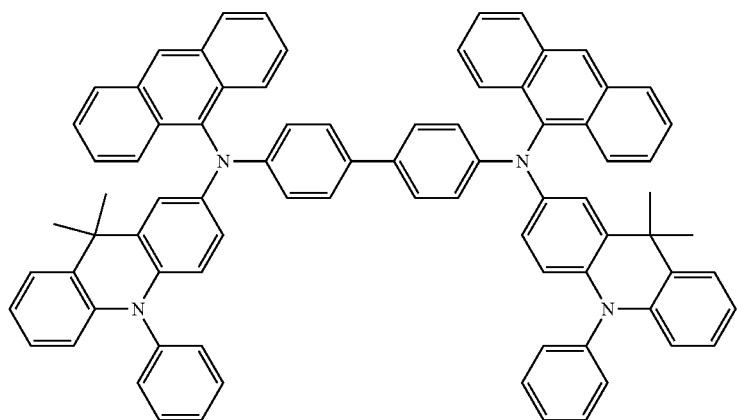
17
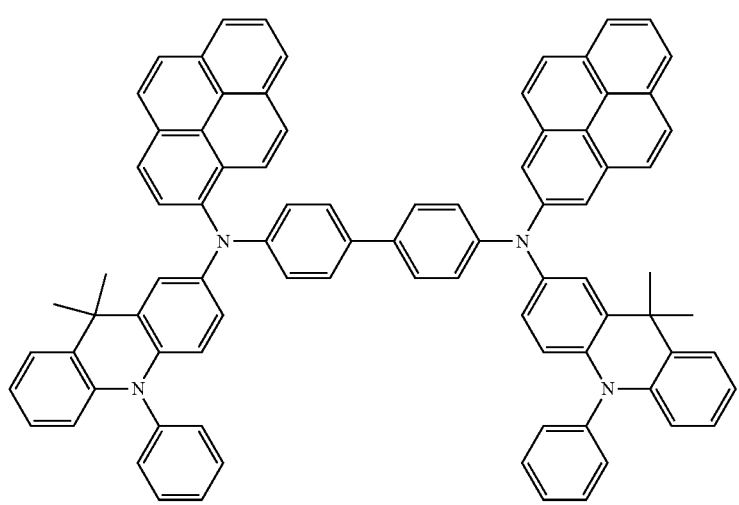

-continued
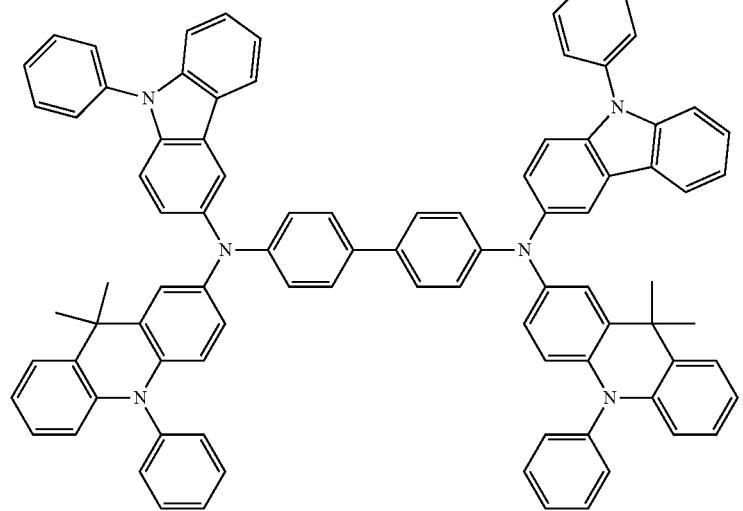
18
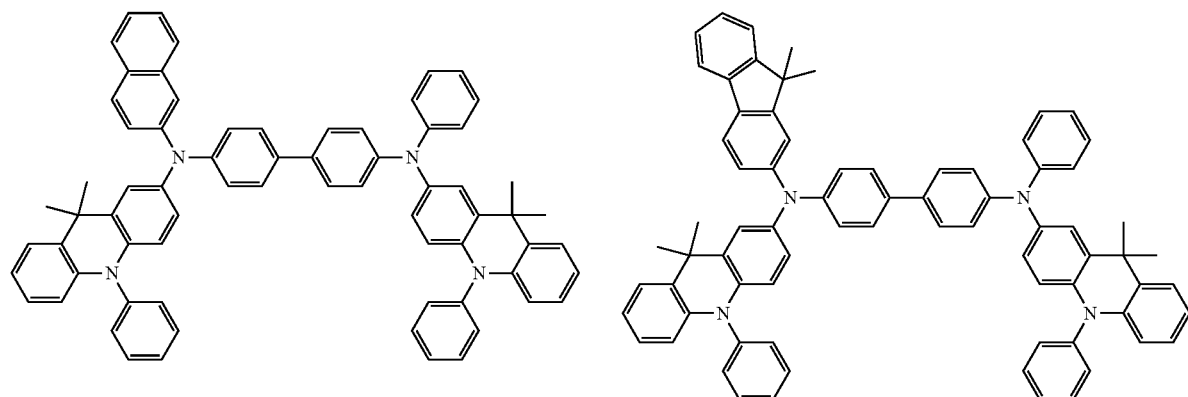
19
20
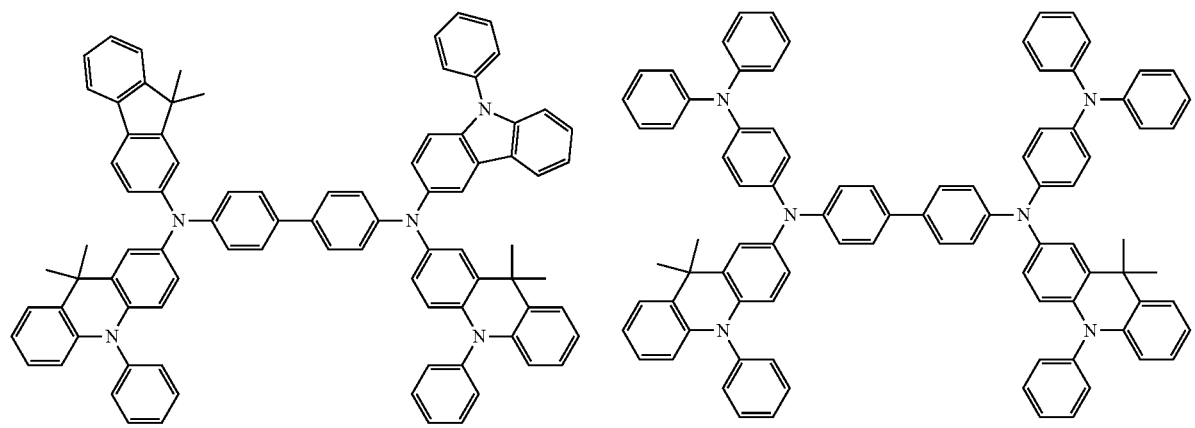
21
22

-continued
23
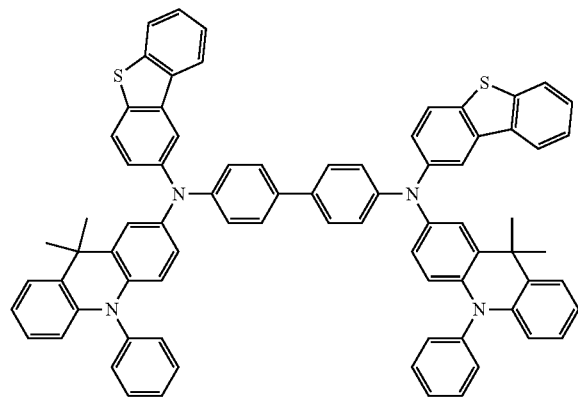
24
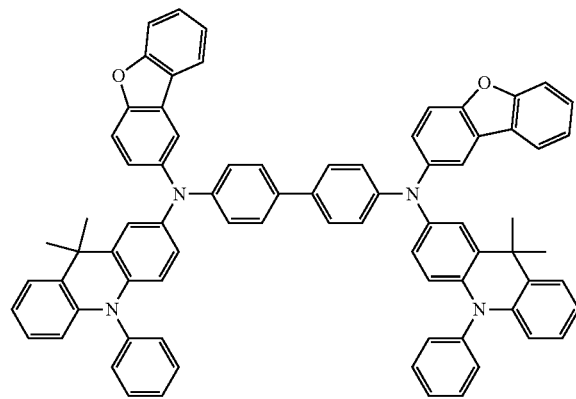
25
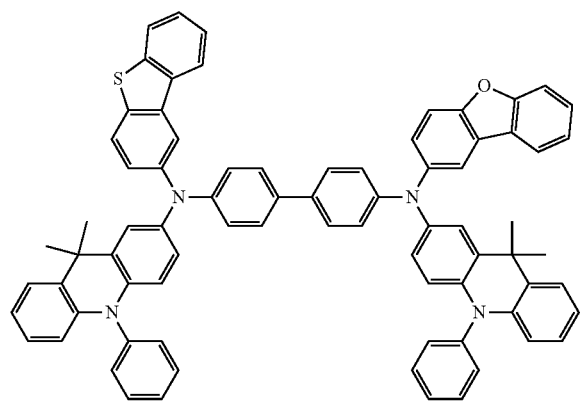
26
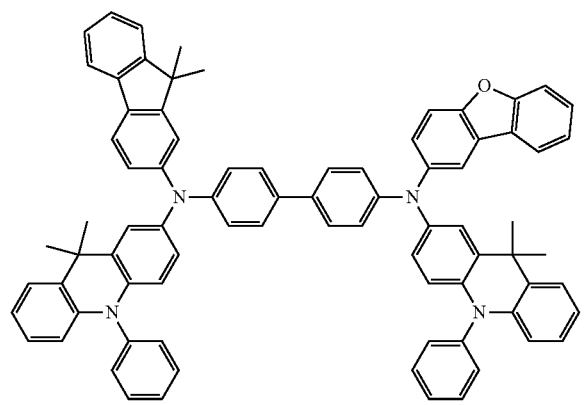
27
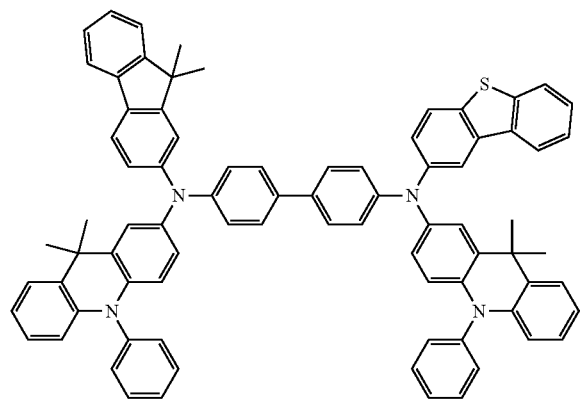
28
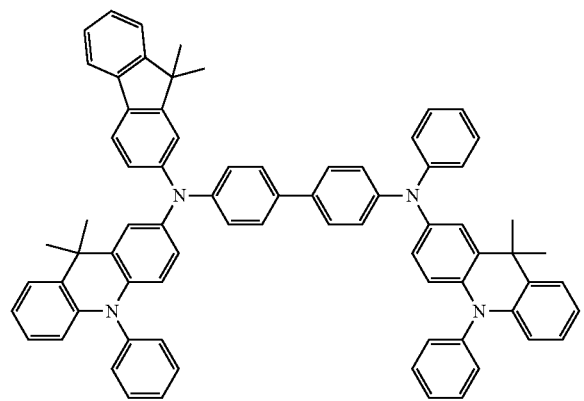

-continued
29
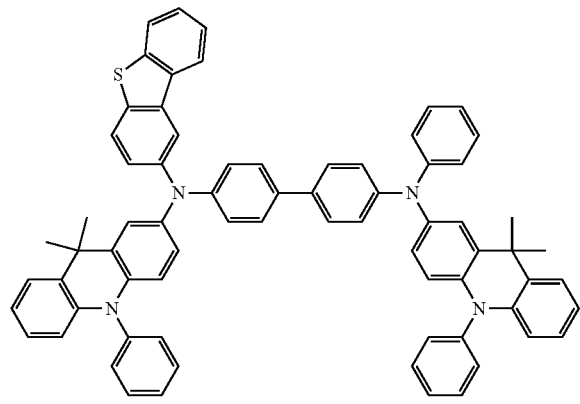
30
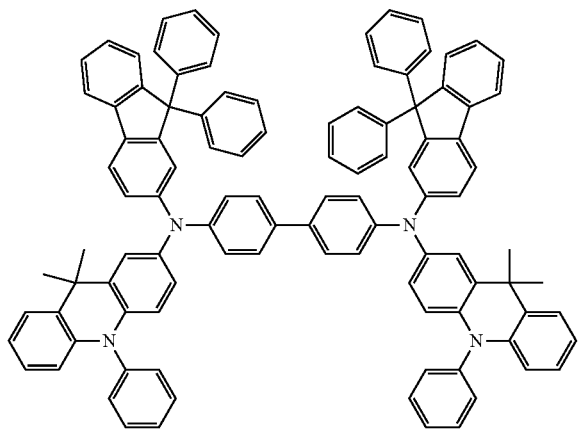
31
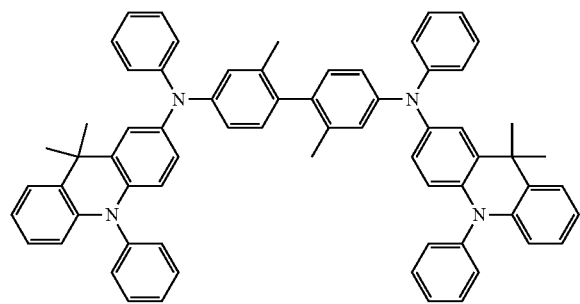
32
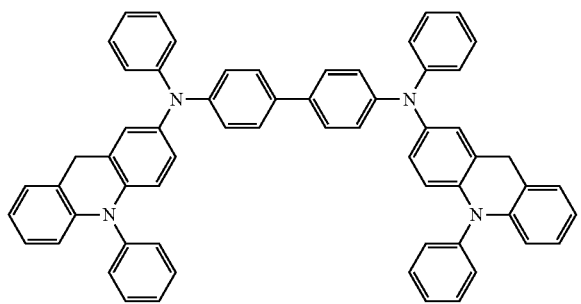
33
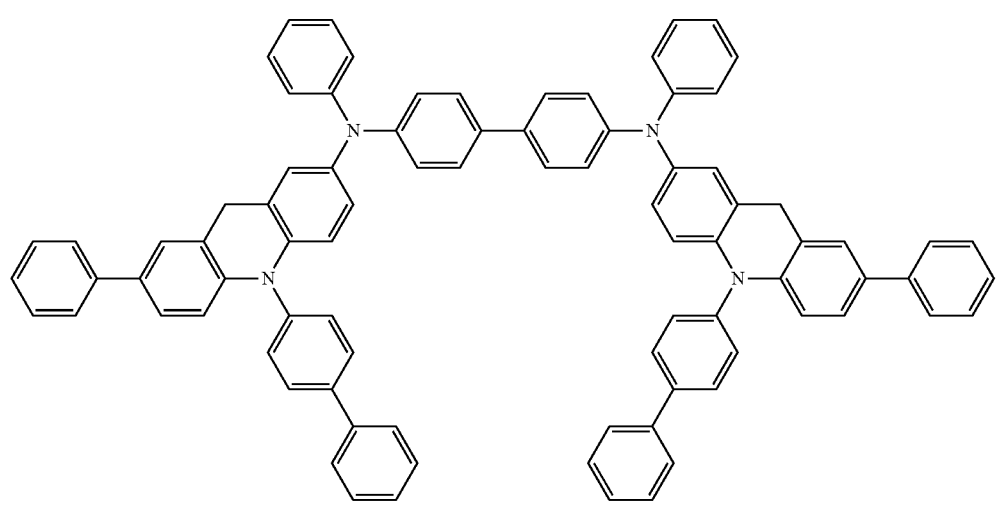

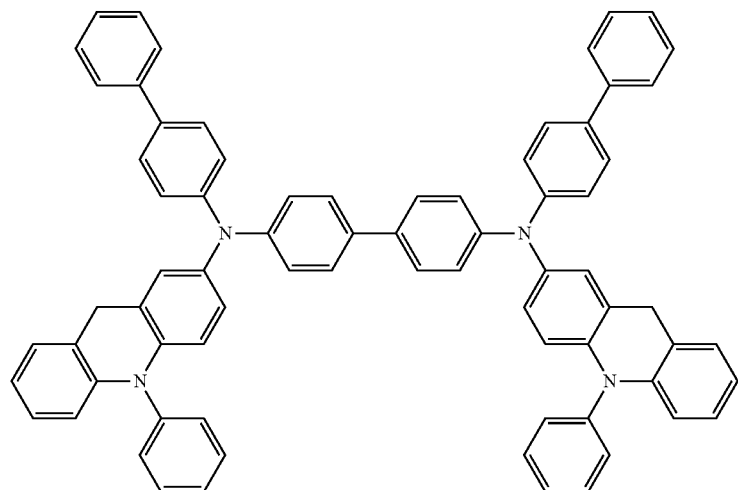
34
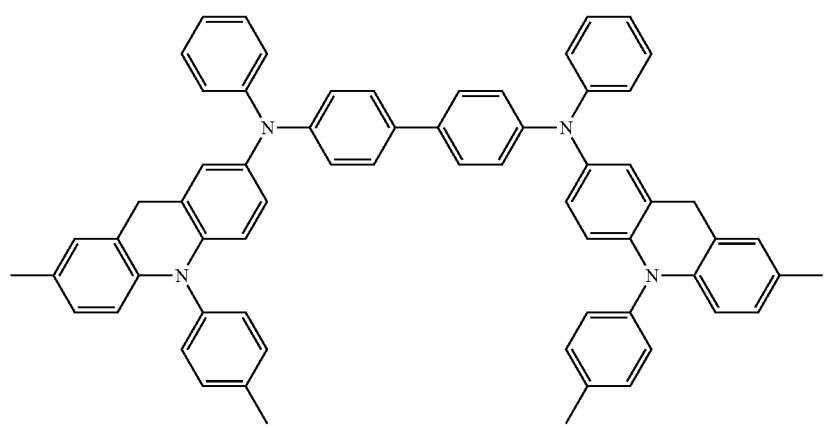
35
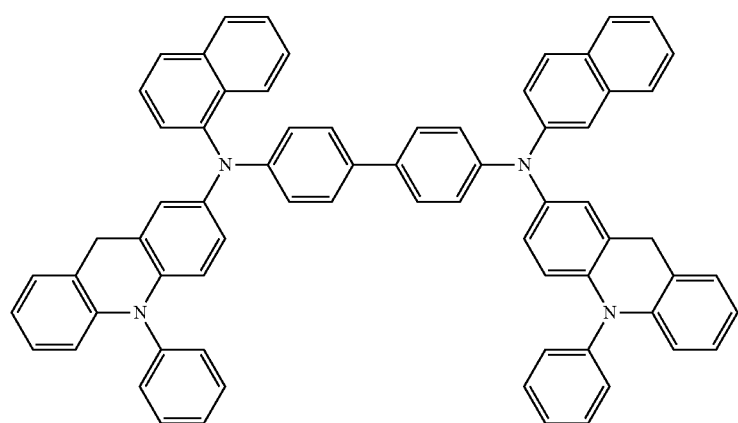
36

-continued
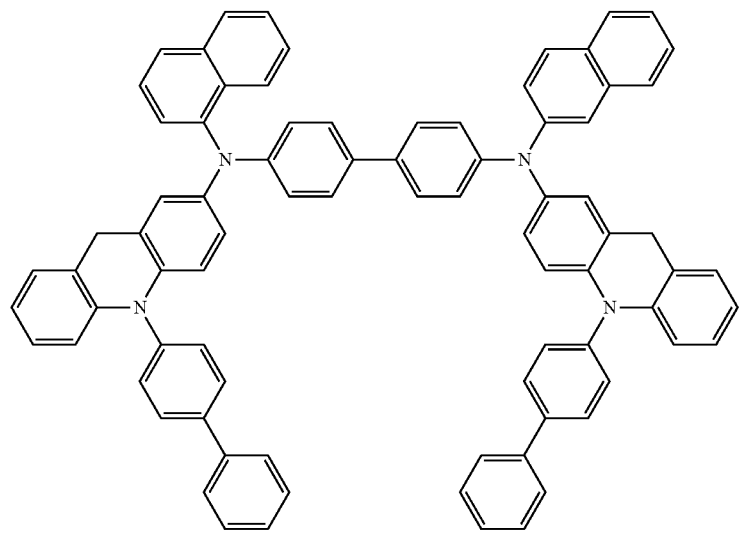
37
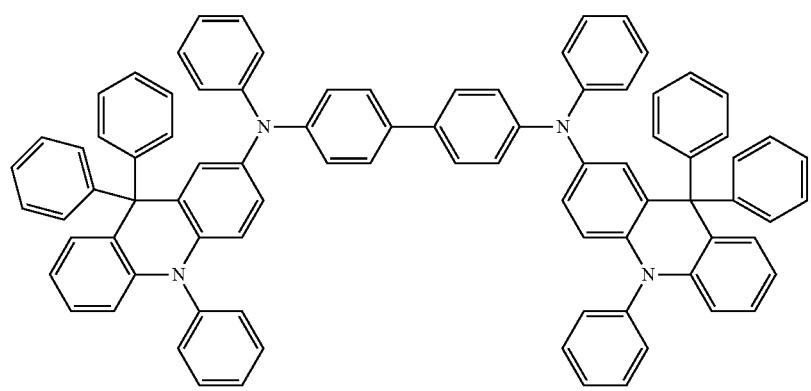
38
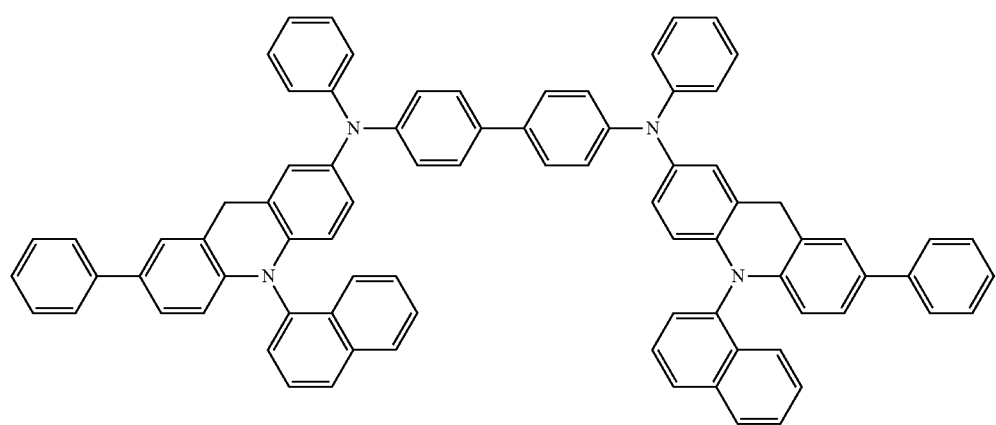
39

-continued

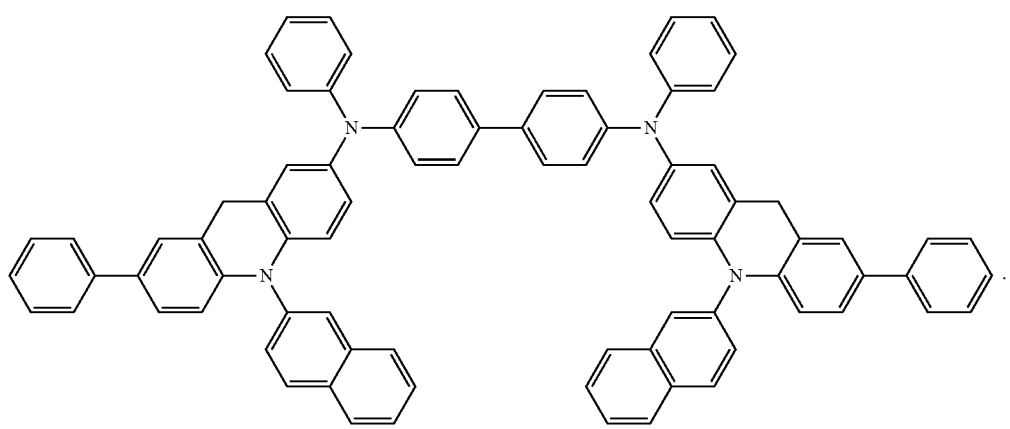

8. The organic electronic material according to claim 7, wherein:
   $R_1$, $R_2$, $R_3$ are independently selected from hydrogen, methyl, phenyl; and
   Ar1-Ar2 independently represent phenyl, naphthyl or biphenyl.

9. An article that includes an organic electronic material, the article comprising:
   the organic electronic material of claim 1; and
   a structure that enables the article to be used in at least one of:
      an organic light-emitting diode (OLED) application;
      organic solar cells;
      organic thin film transistors; and
      organic photoreceptors.

10. An article that includes an organic electronic material, the article comprising:
   the organic electronic material of claim 2; and
   a structure that enables the article to be used in at least one of:
      an organic light-emitting diode (OLED) application;
      organic solar cells;
      organic thin film transistors; and
      organic photoreceptors.

11. An article that includes an organic electronic material, the article comprising:
   the organic electronic material of claim 3; and
   a structure that enables the article to be used in at least one of:
      an organic light-emitting diode (OLED) application;
      organic solar cells;
      organic thin film transistors; and
      organic photoreceptors.

12. An article that includes an organic electronic material, the article comprising:
   the organic electronic material of claim 4; and
   a structure that enables the article to be used in at least one of:
      an organic light-emitting diode (OLED) application;
      organic solar cells;
      organic thin film transistors; and
      organic photoreceptors.

13. An article that includes an organic electronic material, the article comprising:
   the organic electronic material of claim 5; and
   a structure that enables the article to be used in at least one of:
      an organic light-emitting diode (OLED) application;
      organic solar cells;
      organic thin film transistors; and
      organic photoreceptors.

14. An article that includes an organic electronic material, the article comprising:
   the organic electronic material of claim 6; and
   a structure that enables the article to be used in at least one of:
      an organic light-emitting diode (OLED) application;
      organic solar cells;
      organic thin film transistors; and
      organic photoreceptors.

15. An article that includes an organic electronic material, the article comprising:
   the organic electronic material of claim 7; and
   a structure that enables the article to be used in at least one of:
      an organic light-emitting diode (OLED) application;
      organic solar cells;
      organic thin film transistors; and
      organic photoreceptors.

16. An article that includes an organic electronic material, the article comprising:
   the organic electronic material of claim 8; and
   a structure that enables the article to be used in at least one of:
      an organic light-emitting diode (OLED) application;
      organic solar cells;
      organic thin film transistors; and
      organic photoreceptors.

* * * * *